US011065353B2

(12) United States Patent
Ferlic

(10) Patent No.: US 11,065,353 B2
(45) Date of Patent: *Jul. 20, 2021

(54) UNIVERSAL STERILIZING TOOL

(71) Applicant: Michael J. Ferlic, Roseville, MN (US)

(72) Inventor: Michael J. Ferlic, Roseville, MN (US)

(73) Assignee: 1WORLDVISTA MEDICAL, INC., Naples, FL (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/650,698

(22) Filed: Jul. 14, 2017

(65) Prior Publication Data

US 2017/0312377 A1 Nov. 2, 2017

Related U.S. Application Data

(63) Continuation of application No. 14/329,766, filed on Jul. 11, 2014, now Pat. No. 9,707,308, which is a
(Continued)

(51) Int. Cl.
*A61L 2/16* (2006.01)
*A61L 2/235* (2006.01)
(Continued)

(52) U.S. Cl.
CPC ............... *A61L 2/16* (2013.01); *A61L 2/235* (2013.01); *A61M 39/20* (2013.01); *A61B 90/40* (2016.02);
(Continued)

(58) Field of Classification Search
CPC ........ A61L 2/16; A61L 2/235; A61L 2202/24; A61M 39/20; A61M 2005/3106
See application file for complete search history.

(56) References Cited

U.S. PATENT DOCUMENTS 1,374,851 A 4/1921 Hirth
2,030,911 A 2/1936 Borden
(Continued)

FOREIGN PATENT DOCUMENTS

EP 0227219 B1 12/1990
EP 2606930 A1 6/2013
(Continued)

OTHER PUBLICATIONS

International Search Report and Written Opinion of international application No. PCT/US2008/076864, dated Nov. 17, 2008, 18 pp.
(Continued)

*Primary Examiner* — Kevin Joyner
(74) *Attorney, Agent, or Firm* — Sherrill Law Offices, PLLC

(57) ABSTRACT

The sterilizing tool is configured to wipe debris from and to sterilize and/or dry a working end-site of medical device; using a wiping, twisting, dabbing, push/pull, and/or screwing motion around all of the surface aspects of the device to be sterilized. Additionally, the sterilizing tool is configured to form fit to the surfaces of the end-site and to apply an inclusive layer of an anti-pathogenic agent to the inner and outer surfaces of the working end-site. The sterilizing tool may be frictionally engaged with and retained on the working end-site until removed and the end-site is ready for use. The sterilizing tool is intended for a one time, single use, disposable application.

66 Claims, 22 Drawing Sheets

Related U.S. Application Data continuation of application No. 13/445,207, filed on Apr. 12, 2012, now Pat. No. 8,808,637, which is a continuation of application No. 12/624,154, filed on Nov. 23, 2009, now Pat. No. 8,252,247, which is a continuation-in-part of application No. 12/300,717, filed as application No. PCT/US2008/076864 on Sep. 18, 2008, now Pat. No. 8,273,303.

(60) Provisional application No. 61/050,769, filed on May 6, 2008.

(51) Int. Cl.
*A61M 39/20* (2006.01)
*A61M 5/31* (2006.01)
*A61B 90/40* (2016.01)

(52) U.S. Cl.
CPC .. *A61L 2202/24* (2013.01); *A61M 2005/3106* (2013.01)

(56) References Cited

U.S. PATENT DOCUMENTS

| | | |
|---|---|---|
| 3,557,989 A | 1/1971 | Balda |
| 3,661,666 A | 5/1972 | Foster et al. |
| 3,976,311 A | 8/1976 | Spendlove |
| 3,987,930 A | 10/1976 | Fuson |
| 4,340,052 A | 7/1982 | Dennehey et al. |
| 4,354,490 A | 10/1982 | Rogers et al. |
| 4,366,816 A | 1/1983 | Bayard et al. |
| 4,405,312 A | 9/1983 | Gross et al. |
| 4,417,890 A | 11/1983 | Dennehey et al. |
| 4,432,764 A | 2/1984 | Lopez |
| 4,440,207 A | 4/1984 | Genatempo et al. |
| 4,445,896 A | 5/1984 | Gianturco |
| 4,551,137 A | 11/1985 | Osborne |
| 4,551,146 A | 11/1985 | Rogers |
| 4,624,664 A | 11/1986 | Peluso et al. |
| 4,644,966 A | 2/1987 | Ferrari |
| 5,063,049 A | 11/1991 | Billings |
| 5,072,855 A | 12/1991 | Herzig |
| 5,205,821 A | 4/1993 | Kruger et al. |
| 5,242,425 A | 9/1993 | White et al. |
| 5,311,634 A | 5/1994 | Andros |
| 5,353,968 A | 10/1994 | Good, Jr. |
| 5,413,561 A | 5/1995 | Fischell et al. |
| 5,490,736 A | 2/1996 | Haber et al. |
| 5,554,135 A | 9/1996 | Menyhay |
| 5,569,206 A | 10/1996 | Gorman, Jr. et al. |
| 5,620,527 A | 4/1997 | Kramer et al. |
| 5,694,978 A | 12/1997 | Heilmann et al. |
| 5,727,682 A | 3/1998 | Abidin et al. |
| 5,743,892 A | 4/1998 | Loh et al. |
| 5,792,120 A | 8/1998 | Menyhay |
| 5,829,613 A | 11/1998 | Wohlgemuth et al. |
| 5,989,229 A | 11/1999 | Chiappetta |
| 6,003,556 A | 12/1999 | Brugger et al. |
| 6,045,539 A | 4/2000 | Menyhay |
| 6,116,468 A | 9/2000 | Nilson |
| 6,416,323 B1 | 7/2002 | Grenfell et al. |
| 6,517,508 B1 | 2/2003 | Utterberg et al. |
| 6,764,471 B2 | 7/2004 | Lee |
| 6,767,509 B1 | 7/2004 | Griesbach |
| 7,041,083 B2 | 5/2006 | Chu et al. |
| 7,083,605 B2 | 8/2006 | Miyahara |
| 7,198,611 B2 | 4/2007 | Connell et al. |
| 7,282,186 B2 | 10/2007 | Lake, Jr. et al. |
| 7,294,308 B2 | 11/2007 | Kacian et al. |
| 7,682,561 B2 | 3/2010 | Davis et al. |
| 7,763,006 B2 | 7/2010 | Tennican |
| 7,780,794 B2 | 8/2010 | Rogers et al. |
| 7,799,010 B2 | 9/2010 | Tennican |
| 7,972,322 B2 | 7/2011 | Tennican et al. |
| 8,065,773 B2 | 11/2011 | Vaillancourt et al. |
| 8,122,519 B2 | 2/2012 | Schmelzer et al. |
| 8,162,899 B2 | 4/2012 | Tennican et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,252,247 B2 | 8/2012 | Ferlic |
| 8,262,643 B2 | 9/2012 | Tennican |
| 8,273,303 B2 | 9/2012 | Ferlic et al. |
| 8,328,767 B2 | 12/2012 | Solomon et al. |
| 8,336,152 B2 | 12/2012 | Vaillancourt et al. |
| 8,343,112 B2 | 1/2013 | Solomon et al. |
| 8,388,894 B2 | 3/2013 | Colantonio et al. |
| 8,628,501 B2 | 1/2014 | Hadden |
| 8,784,388 B2 | 7/2014 | Charles et al. |
| 8,808,637 B2 | 8/2014 | Ferlic |
| 8,828,327 B2 | 9/2014 | Colantonio et al. |
| 9,078,992 B2 | 7/2015 | Ziebol et al. |
| 9,561,298 B2 | 2/2017 | Ferlic et al. |
| 9,572,904 B2 | 2/2017 | Ferlic |
| 9,707,308 B2 | 7/2017 | Ferlic et al. |
| 2002/0168530 A1 | 11/2002 | Tingey et al. |
| 2003/0017073 A1 | 1/2003 | Eckhardt et al. |
| 2004/0031120 A1 | 2/2004 | Cherian |
| 2005/0045031 A1 | 3/2005 | Rajagopalan et al. |
| 2005/0075611 A1* | 4/2005 | Hetzler ............... A61L 2/0011 604/192 |
| 2005/0124970 A1 | 6/2005 | Kunin et al. |
| 2005/0242204 A1 | 11/2005 | Ness et al. |
| 2006/0030827 A1 | 2/2006 | Raulerson et al. |
| 2007/0106205 A1 | 5/2007 | Connell et al. |
| 2007/0112333 A1 | 5/2007 | Hoang et al. |
| 2007/0225660 A1 | 9/2007 | Lynn |
| 2007/0282280 A1 | 12/2007 | Tennican et al. |
| 2008/0019889 A1 | 1/2008 | Rogers et al. |
| 2008/0021381 A1 | 1/2008 | Lurvey et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0107564 A1 | 5/2008 | Sternberg et al. |
| 2008/0132880 A1 | 6/2008 | Buchman et al. |
| 2008/0177250 A1 | 7/2008 | Howlett |
| 2008/0235888 A1 | 10/2008 | Vaillancourt et al. |
| 2009/0028750 A1 | 1/2009 | Ryan et al. |
| 2009/0137969 A1 | 5/2009 | Colantonio et al. |
| 2009/0205151 A1 | 8/2009 | Fisher et al. |
| 2009/0297400 A1 | 12/2009 | Cady et al. |
| 2010/0000040 A1 | 1/2010 | Shaw et al. |
| 2010/0003067 A1 | 1/2010 | Shaw et al. |
| 2010/0050351 A1 | 3/2010 | Colantonio et al. |
| 2010/0064456 A1 | 3/2010 | Ferlic |
| 2010/0083452 A1 | 4/2010 | Vaillancourt et al. |
| 2010/0200017 A1 | 8/2010 | Kerr et al. |
| 2011/0030726 A1 | 2/2011 | Vaillancourt et al. |
| 2011/0054440 A1 | 3/2011 | Lewis |
| 2011/0184382 A1 | 7/2011 | Cady |
| 2011/0265825 A1 | 11/2011 | Rogers et al. |
| 2011/0314619 A1 | 12/2011 | Schweikert |
| 2012/0016318 A1 | 1/2012 | Hoang et al. |
| 2012/0022469 A1 | 1/2012 | Alpert |
| 2012/0302997 A1 | 11/2012 | Gardner et al. |
| 2013/0164189 A1 | 6/2013 | Hadden |
| 2013/0197485 A1 | 8/2013 | Gardner et al. |
| 2014/0188089 A1 | 7/2014 | Midgette et al. |
| 2014/0228773 A1 | 8/2014 | Burkholz |
| 2014/0261558 A1 | 9/2014 | Rogers et al. |
| 2015/0343174 A1 | 12/2015 | Ziebol et al. |

FOREIGN PATENT DOCUMENTS

| | | |
|---|---|---|
| JP | 1284222 A | 11/1989 |
| WO | 2007044760 A2 | 4/2007 |
| WO | 2007137056 A2 | 11/2007 |
| WO | 2008089196 A2 | 7/2008 |
| WO | 2008100950 A2 | 8/2008 |
| WO | 2008140807 A4 | 11/2008 |
| WO | 2009123709 A2 | 10/2009 |

(56) References Cited

FOREIGN PATENT DOCUMENTS

OTHER PUBLICATIONS

The Curos(TM) Port Protector. Simply Changing Infection Control Practice. Printout from http://www.iveramed.com/v_access_ports_infection_control.html, copyright 2008, originally accessed in 2008, 1 page.
U.S. Appl. No. 13/445,207, filed Apr. 12, 2012.
Flourney, How Does Alcohol Kill Bacteria?, sciencing.com, retrieved Mar. 5, 2020, from https://sciencing.com/alcohol-kill-bacteria-5462404.html.

* cited by examiner

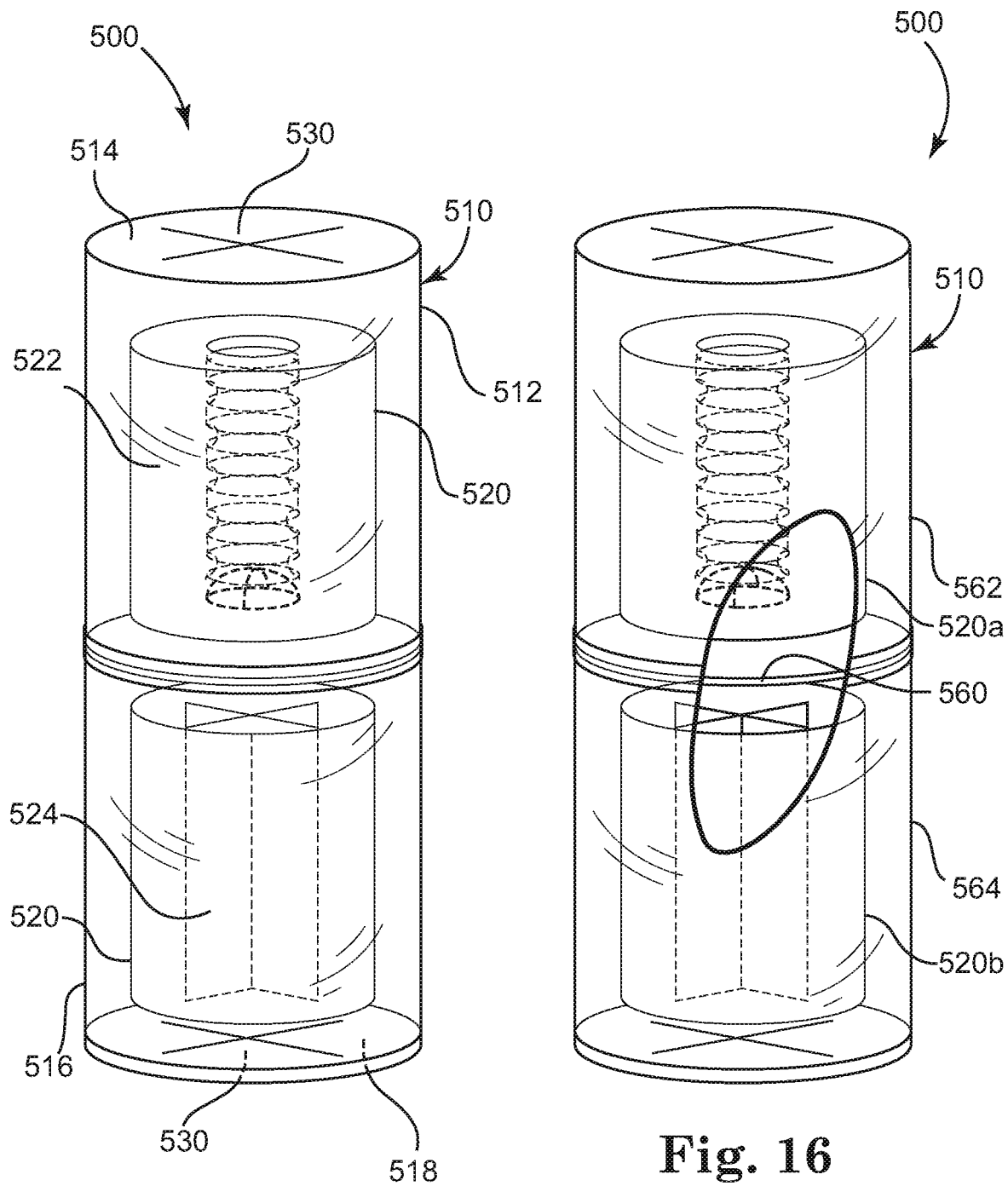

UNIVERSAL STERILIZING TOOL

CROSS-REFERENCE TO RELATED APPLICATIONS

This application is a continuation of U.S. application Ser. No. 14/329,766, filed Jul. 11, 2014, which is a continuation of U.S. application Ser. No. 13/445,207, filed Apr. 12, 2012, which is a continuation of U.S. application Ser. No. 12/624,154, filed Nov. 23, 2009, which is a continuation-in-part of U.S. application Ser. No. 12/300,717, filed Nov. 13, 2008, which is 371 application of International Application No. PCT/US2008/076864, filed Sep. 18, 2008, which claims priority to U.S. Provisional Application No. 61/050,769, filed May 6, 2008, all of which are incorporated herein by reference in their entirety for all purposes.

TECHNICAL FIELD

The present invention relates to devices and methods for sterilizing the medical connection sites of luer connections, luer compatible components, catheter hubs, and other medical connections and access ports. More particularly, the present invention relates to a contoured sterilizing element that is configured to form-fit to the various shapes and working aspects of the component being sterilized.

BACKGROUND

Mating luer connections, needleless connectors, and needle access ports serve as a conduit for administering medication to a patient by the joining of their mutual complimentary components. Prior to connecting two luer compatible components together, it is important to sterilize the connection end-sites. Typically, the connection end-sites are sterilized by wiping each site with an antiseptic wipe. Contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g. needle-less connector having assembled components such as a housing, seals, valve or septum) requires an awareness to effectively sterilize and thoroughly kill those pathogens that would otherwise make an already sick patient worse. The wiping and sterilizing of the connection end-sites must be done for a specified amount of time and accuracy to achieve a "kill of microbes" prior to the luer compatible components being connected together to reduce the risk of infection to the patient. This is also true for needle access ports or other connections. Without this simple precautionary step of sterilizing the working end-sites, patients are at a greater risk of contracting an infection.

The current method for sterilizing a connection end-site, catheter hub, needle access port, or needleless connector employs an antiseptic towelette that comes in a small foil packet and is commonly used throughout hospitals, clinics, and home healthcare. The foil packet in which the antiseptic towelette comes in must be torn open and the towelette lifted out with gloved hands. The towelette is a small folded sheet of fibrous, non-woven material that contains isopropyl alcohol. The clinician cannot adequately use the towelette to wipe the various complex surfaces, edges, threads, lumen, septum of a working end-site due to the towelette's small size and flimsy characteristics. Thus, that which should be a routine precautionary step to maintain sterility is unfortunately either ignored or not adequately performed to prevent patient infection.

SUMMARY

According to various embodiments, the present invention is a contoured, pre-moistened anti-pathogenic sterilizing element for wiping medical luer compatible connector end-sites, needleless connector end-sites, and/or needle access port end-sites. According to some embodiments, the sterilizing element is pre-shaped to contour to the outer and inner surfaces of the working end-site of a medical device such that it contacts the outer and inner surfaces of the working site. A wiping and/or a twisting motion is used to wipe debris from and apply a layer of an anti-pathogenic agent to the site. In some embodiments, the sterilizing element is contained in a flexible tubular or rectangular housing.

According to other embodiments, the present invention is a universally adaptable, contoured sterilizing element that is contained within a small ergonomic housing configured to be held in the fingers of one hand. In some embodiments, the housing may be opened by using the fingers of one hand to squeeze the lateral sides, or by forcibly pushing a site end through a sealed membrane or frangible lid to engage the contoured sterilizing element. In other embodiments, the cover can be physically removed from the top of the housing to access the contoured sterilizing element contained within the housing. In other embodiments, the sterilizing element may be left engaged with the working end-site until the end-site is ready for use.

According to some embodiments, the present invention is a sterilizing element for cleaning and sterilizing outer and inner surfaces of a working end-site of a medical device. The sterilizing element includes an anti-pathogenic agent. According to some embodiments, the sterilizing element may be pre-moistened or impregnated with the anti-pathogenic agent. According to other embodiments, the anti-pathogenic agent may be bonded to a surface of the sterilizing element. The sterilizing element includes a first end and a second end and a recessed portion configured to receive the working end-site of the medical device therein. Additionally, the recessed portion includes an inner surface configured to contour to and contact the outer surfaces of the working end-site of the medical device and a raised base portion configured to contact and engage the inner surfaces of the working end-site of the medical device.

According to another embodiment, the sterilizing element includes first and second ends and a recessed portion configured to inwardly receive the working end-site of the medical device. In certain embodiments, the recessed portion includes: a base portion configured to contact a distal end of the working end-site; an inner surface configured to contour and form-fit to the outer surfaces of the working end-site of the medical device; and an inner diameter that tapers down from the first end to the second end of the sterilizing element. According to some embodiments, the sterilizing element may be pre-moistened or impregnated with the anti-pathogenic agent. According to other embodiments, the anti-pathogenic agent may be bonded to a surface of the sterilizing element.

In other embodiments, the present invention is a sterilizing device for wiping and sterilizing outer and inner surfaces of a working end-site of a medical device including a housing and a sterilizing element secured and contained within the housing. In some embodiments, the housing includes at least one end adapted to be opened, and sidewalls having an outer surface. In some embodiments, the sterilizing element includes a first end, a second end, and a recessed portion configured to receive and engage the outer surfaces of the working end-site. In certain embodiments, the recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

In some embodiments, the at least one end adapted to be opened includes a seal adapted to be transitioned from a closed configuration to an open configuration by the application of an inward pressure applied to the sidewalls of the housing. In other embodiments, the at least one end adapted to be opened includes a lid adapted to be removed from the housing by the application of an inward pressure applied to the sidewalls of the housing.

In certain embodiments, the housing includes an envelope of a flexible material and wherein the at least one end comprises a removable portion. In further embodiments, the housing includes an envelope of a flexible material having a lining, the lining comprising the sterilizing element according to the various embodiments of the present invention.

In some embodiments, the at least one end adapted to be opened includes a frangible lid. According to various embodiments, the frangible lid can be made of plastic, mylar, foil, laminated foil, laminate, or other similar material. In other embodiments, the at least one end adapted to be opened includes a pre-scored lid. In still other embodiments, the at least one end comprises a peel-away lid. According to further embodiments, the housing includes a protective cover secured adjacent to the at least one end adapted to be opened.

In some embodiments, the housing further includes a removable cover secured over the at least one end adapted to be opened. According to some embodiments, the removable cover includes a second sterilizing element contained and secured within the removable cover. The sterilizing element includes a first end and a second end and a recessed portion configured to receive and contact the outer surfaces of the working end-site. The recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

According to some embodiments, the present invention is a dual-ended sterilizing device including an elongated housing comprising a first portion having a first end adapted to be opened and a second portion having a second end adapted to be opened, and a first sterilizing element contained and secured within the housing. The sterilizing element includes at least one end configured to inwardly receive a working end-site of a medical device therein to conform to and contact at least the outer surfaces of the working end-site. According to some embodiments, the sterilizing element may be pre-moistened or impregnated with the anti-pathogenic agent. According to other embodiments, the anti-pathogenic agent may be bonded to a surface of the sterilizing element.

According to some embodiments, the sterilizing element includes a single, continuous foam piece extending from the first end of the first portion of the housing to the second end of the second portion of the housing. The continuous foam piece generally includes a first end and a second end. Each end of the continuous foam piece is configured to inwardly receive the working end-site therein, and to contour to at least the outer surfaces of the working end-site of the medical device. According to some embodiments, the sterilizing element may be pre-moistened or impregnated with the anti-pathogenic agent. According to other embodiments, the anti-pathogenic agent may be bonded to a surface of the sterilizing element.

According to some embodiments, the dual ended sterilizing device further includes a partition separating the first portion of the housing from the second portion of the housing. The first sterilizing element is secured within the first portion of the housing. In some embodiments, the dual ended sterilizing device includes a second sterilizing element contained and secured within the second portion of the housing. According to various embodiments, the second sterilizing element includes an anti-pathogenic agent and at least one end configured to inwardly receive and conform to at least the outer surfaces of the working end-site. In other embodiments, a sterile drying element can be contained and secured within the second portion of the housing. The sterile drying element can be configured to inwardly receive and conform to at least the outer surfaces of the working end-site. In certain embodiments, the drying element may be left engaged with the working end-site until the site is ready for use. In still other embodiments, the dual ended sterilizing device includes a female luer connector secured to the partition and contained within the second portion of the housing. The female luer connector can be adapted to connect to any one of a male luer lock, slip luer, or thread luer connector.

According to some embodiments, the present invention provides a method of wiping, drying, and sterilizing a medical device including a working end-site having inner and outer surfaces including: providing a sterilizing element comprising an anti-pathogenic agent, and a recessed portion having an inner surface configured to contour to the outer surfaces of the working end-site and a raised portion configured to contact and engage the inner surfaces of the working end-site; inserting the working end-site into the recessed portion of the sterilizing element to engage the working end-site therein; wiping and sterilizing the working end-site located within the recessed portion, removing the working end-site from the sterilizing element, and air-drying the working end-site for a period of time. In some embodiments, the method further includes disposing of the sterilizing element after the initial use.

In some embodiments, the method further includes forcibly engaging the working end-site through the at least one end adapted to be opened to access the sterilizing element contained within the housing. In other embodiments, the method further includes squeezing the sidewalls of the housing to transition the at least one end from a closed configuration to an open configuration to access the sterilizing element contained within the housing. In certain embodiments, the at least one end of the housing may be transitioned from a closed configuration to an open configuration using the fingers on a single hand.

In some embodiments, the method further includes compressing the sterilizing element to expel the anti-pathogenic agent from the sterilizing element and onto the working end-site. In some, the step of compressing the sterilizing element includes engaging the working end-site in the recessed portion of the sterilizing element. In other embodiments, the step of compressing the sterilizing element includes squeezing the sidewalls of the housing to expel the anti-pathogenic agent from the sterilizing element onto the working end-site.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 15 is an isometric view of a dual sided sterilizing device according to another embodiment of the present invention.

FIG. 16 is an isometric view of a dual sided sterilizing device according to yet another embodiment of the present invention.

DETAILED DESCRIPTION

All medical luers and all medical device ends need to be sterilized prior to use. The term "luer" is well known in the medical field and in the art and is used here (luer hub, male luer, female luer, slip luer) to mean mating structures, with or without threads, that allows two mating luer devices, or luer compatible components, to be joined for fluid communication. The term "site," "end-site" or "site end" is used interchangeably and is used here to be understood to mean any and all working ends and/or sites including, but not limited to, a luer, luer hub (e.g. catheter hub), luer compatible component, needle access port, needleless connector, or septum. According to various embodiments, the present invention is a tool for effectively sterilizing and wiping debris from all surfaces of a working end including, but not limited to, threads, sides, edges, inner lumens, septums, and needle access ports.

Figure 1:
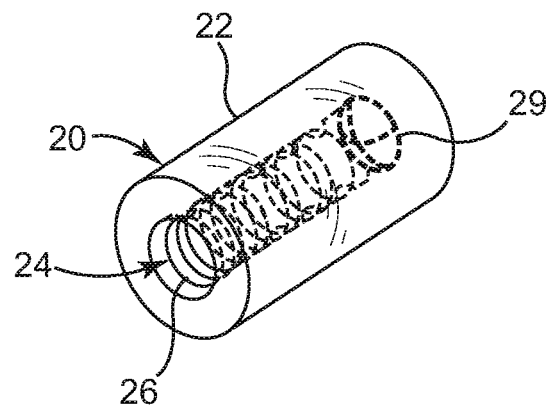
FIG. 1 is an isometric view of a contoured sterilizing element provided in accordance with an embodiment of the present invention.
Figure 2A:
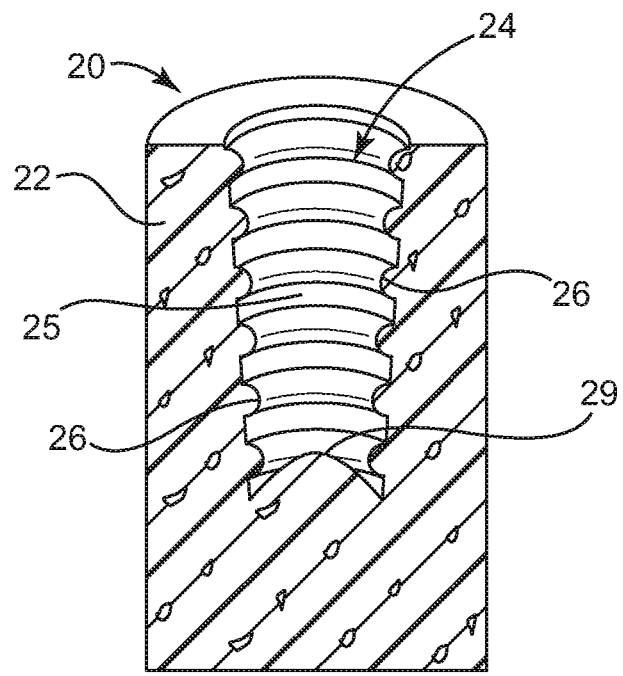
FIG. 2A-2C are cross-sectional views of a contoured sterilizing element in accordance with various embodiments of the present invention.
Figure 2B:
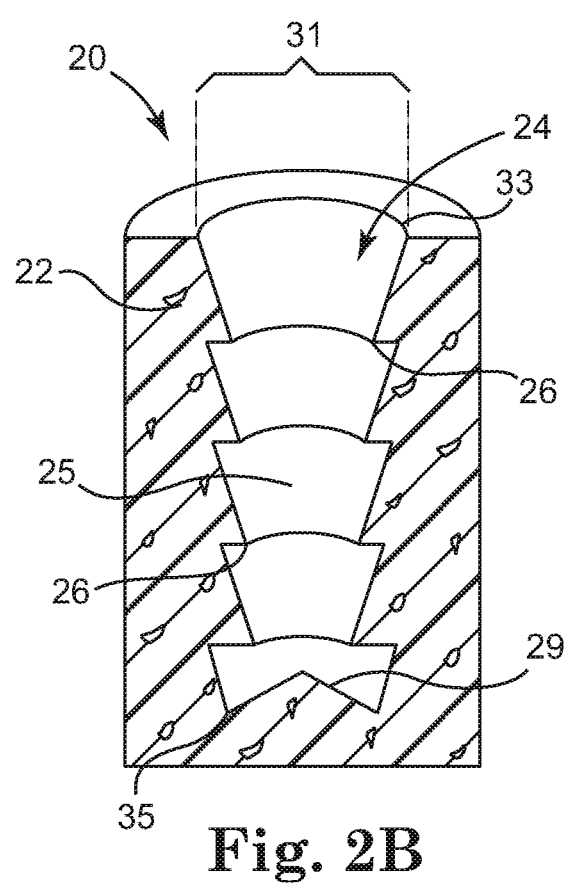
Figure 2C:
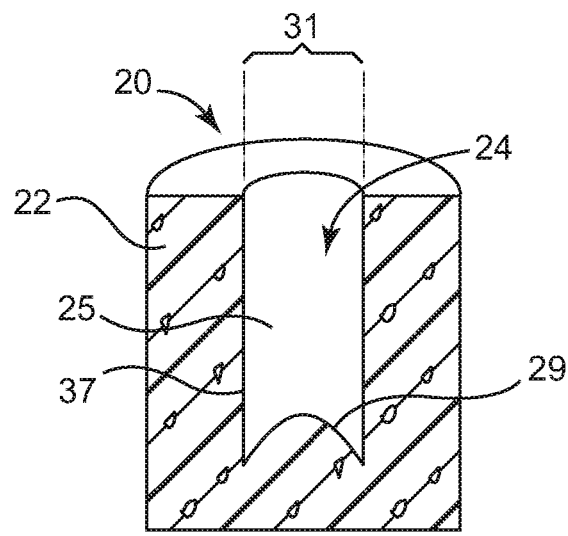

FIG. 1 is an isometric view of a contoured sterilizing element 20 provided in accordance with various embodiments of the present invention. FIGS. 2A-2C are cross-sectional views of the contoured sterilizing element 20, as shown in FIG. 1, according to various embodiments of the present invention. The sterilizing element 20 is configured to wipe debris from and to sterilize and/or dry a working end-site of a catheter hub, luer connector, luer component, and/or access port using a wiping, twisting, dabbing, push/pull and/or screwing motion around all of the surface aspects of the device to be sterilized. Additionally, the sterilizing element 20 is configured to apply an inclusive layer of an anti-pathogenic agent to the inner and outer surfaces of the working end-site. An inclusive layer, as used herein, is a layer of the anti-pathogenic agent applied via the contoured aspects of the sterilizing element which contacts all accessible inner and outer surfaces of the working end-site and contains an amount of the pathogenic agent sufficient to effectively sterilize the working end-site of the medical device. The contoured sterilizing element 20 is intended for a one time, single use, disposable application.

The sterilizing element 20 can be made from a variety of materials including, but not limited to, non-woven, particulate-free absorbent foams, natural or synthetic sponges, or other suitable materials, both semi-flexible or semi-ridged, known to those of skill in the art. In some embodiments, the contoured sterilizing element 20 includes an absorbent foam article 22. In other embodiments, the contoured sterilizing element 20 is formed from an absorbent, viscoelastic resilient foam or silicone rubber.

According to some embodiments, the absorbent material can be pre-shaped or pre-molded such that it is configured to contour to the surfaces of the working end to be sterilized. For example, in some embodiments, the sterilizing element 20 can be contoured and pre-shaped such that it is configured to form-fit over the working end-site of a medical connector, catheter hub, luer compatible connector, luer component, and/or needle access port for efficient wiping and sterilizing. In other embodiments, the sterilizing element 20 can be shaped to contour to and engage an inner lumen, septum, port, and/or needleless injection site. In other embodiments, a micropatterned or microtextured surface on the sterilizing element 20 provides an additional refinement to the contour sterilizing tool for contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g. needle-less connector having assembled components such as a housing, seals, valve or septum). The microtexturing or micropatterning can include any one of a number of ridges, bumps, surface roughing, rings, concentric circles, lattice features and the like. In yet other embodiments, the sterilizing element 20 is configured to engage a working end-site of a medical device such that a friction fit is created between the sterilizing element 20 and the end-site of the medical device. The sterilizing element 20 can remain frictionally engaged with the working end-site until ready for use. According to another embodiment, the absorbent foam material is sufficiently resilient such that it conforms to the surfaces of the working end-site when the working end-site is depressed into the absorbent material.

According to various embodiments, the absorbent material includes an anti-pathogenic agent including any one of an antiseptic, disinfectant, microbiocidal, or combinations thereof to kill pathogens on the surfaces of the device. According to one embodiment, an anti-pathogenic agent is a dry agent bonded to the surfaces of the sterilizing element. According to another embodiment, the sterilizing element is impregnated with an anti-pathogenic agent. For example, the sterilizing element may be impregnated with an oligodynamic metal. An oligodynamic metal is a metal shown to have anti-bacterial properties even in minute quantities. Exemplary oligodynamic metals include, but are not limited to, the following: gold, zinc, copper, and cerium. According to one embodiment, the sterilizing element may be impregnated with silver. In other embodiments, the absorbent material is pre-moistened with at least one anti-pathogenic agent. Exemplary anti-pathogenic agents include, but are not limited to, the following: isopropyl alcohol, povidone iodine, chlorhexidine gluconate, and other useful anti-pathogenic agents known to those of skill in the art. Additionally, depending on the anti-pathogenic agent used, a sufficient amount of anti-pathogenic agent can be incorporated into microporous surface of the absorbent material to achieve an acceptable ratio of "anti-pathogenic agent to dry-time," wherein a sufficient amount of anti-pathogenic agent is impregnated into the microporous surface and is used to adequately disinfect the site end while at the same time achieving a fast drying rate. The end-site connector devices should be sterile, dry, and free of anti-pathogenic residue, or additionally provide an anti-pathogenic residue that would maintain the sterility of the end-site until use by the clinician and be non-toxic and compatible to both the patient and the end-site material since the connector end-sites complete the pathway of medication into the patient's body prior to their connection. According to one embodiment, the drying rate after the anti-pathogenic agent has been applied to the working end-site is less than about 15 seconds. In other embodiments, the drying rate is less than about 10 seconds. In still other embodiments, the drying rate is less than about 7 seconds.

In some embodiments, the working end-site undergoes a visual change in appearance when contacted with the anti-pathogenic agent contained within the sterilizing element 20. For example, in some embodiments, the sterilizing element 20 releases the anti-pathogenic agent upon contact with the working end-site of the medical device, wetting the surface with the anti-pathogenic agent and causing a visual change in the end-site due to a microtextured microporous (e.g., a polymeric porous permeable polymer), micropatterned, bonded or solvatochromic dyed surface (e.g., merocyanine dye or Reichardt's dye) of the end-site. Exemplary surfaces of a working end-sit adapted to undergo a visual change upon contact with an anti-pathogenic agent or other change initiating reactant are generally shown and described in U.S. Published Application No. 2008/0021381, entitled "Medical Fluid Access Device with Antiseptic Indicator," the entirety of which is incorporated by reference herein for all purposes. As a result of contact with the anti-pathogenic agent, the working end-site can visually change from a first state to a second state such as, for example, from visually light to visually dark or from a dark surface to a light surface over time due to exposure to the anti-pathogenic agent or from a wetted surface to a dry surface.

In other embodiments, the sterilizing element 20 itself can be adapted to undergo a visual change. For example, the sterilizing element 20 is impregnated with an anti-pathogenic agent such as IPA (isopropyl alcohol) and can visually change from a darker appearance when contact is first made with the working end-site to a lighter appearance as when the sterilizing element 20 is left in place on the working end-site and the anti-pathogenic agent dries and/or evaporates. In some embodiments, the sterilizing element 20 can include a micropatterned (such fine lines, cracks), microporous or microtextured surface, such as described above, that is adapted to undergo the visual change.

In yet another embodiment, the sterilizing element 20 is impregnated with a visual change reactant that when applied to working end-site indicates that the end-site has been contacted with the anti-pathogenic agent and sterilized. In some embodiments, the visual change reactant can undergo a transition to indicate that the working-end site dried. Exemplary visual change reactants can include a number of dyes suitable for this purpose known to those of skill in the art. In some embodiments, the visual change observed on either the surface of the working end-site or the sterilizing element 20 itself, as described above, can be a visual color change.

In further embodiments, the sterilizing element 20 can be translucent or even transparent such that a visual change in the working end-site or even the sterilizing element 20 can be easily and readily observed by the user through the sterilizing element 20 to the end-site. For example, in one embodiment a the translucent/transparent sterilizing element 20 including a microtextured, micropatterned or microporous surface, such as described above, provides the clinician with a view of refraction that occurs when the wetted, resilient surface of the sterilizing element 20 contacts the harder, more ridged surfaces of the end-site causing a visual change to occur from a darker appearance when contact is first made to a lighter appearance following the removal of the sterilizing element 20 and the end-site allowed to dry.

FIGS. 2A-2B are cross-sectional views of a sterilizing element 20, according to various embodiments of the present invention. According to some embodiments, the contoured sterilizing element includes an absorbent foam piece 22 having a recessed portion 24 including an inner surface 25 configured for receiving the working end-site of a medical device to be sterilized therein. According to one embodiment, the recessed portion 25 is configured such that the working end-site can be inserted to a depth of approximately 10 mm. In other embodiments, the recessed portion 25 is configured such that the working end-site can be inserted into the recessed portion 25 by a depth of about 5 mm to about 7 mm. In yet another embodiment, the working end-site may be inserted into the recessed portion 25 by a depth of about 3 mm.

As shown in FIGS. 2A and 2B, the recessed portion 24 can include a plurality of raised structures 26 formed on the inner surface 25 of the recessed portion 24. The raised structures 26 project into the recessed portion, and are configured to engage the threads, sides, and/or edges on the working end-site. In some embodiments, the raised structures 26 can include ridges, flanges, and/or threads, as shown in FIG. 2A, steps as shown in FIG. 2B, or combinations thereof. According to a further embodiment, as shown in FIG. 2B, the raised structures 26 provided on the inner surface 25 of the recessed portion 24 provide an inner diameter 31 that tapers down from a first end 33 to a second end 35 of the sterilizing element 20. These raised structures 26 located on the inner surface 25 of the recessed portion or cavity 24 of the sterilizing element 20 facilitate the effective sterilization of all surfaces of the working end-site of a first connection device prior to the attachment with a complimentary second connection device.

Additionally, in some embodiments the recessed portion 24 can include a raised base portion 29 configured to project into and engage the inner luer lumen and/or septum of a needleless connector or port end. The raised base portion can have a number of configurations. For example, the raised base portion 29 can be configured as any one of a nipple, bump, nub, tine, or other similar projection.

FIG. 2C is a cross-sectional view of a sterilizing element 20 according to yet another embodiment of the present invention. As shown in FIG. 2C the sterilizing element 20 includes a generally, cylindrical absorbent foam piece 22 having a recessed portion 24. The cylindrical foam piece 22 can be contoured and shaped so that it "form-fits" over the working end-site of a luer compatible connector, medical device connector component, and/or needle access port for efficient wiping and sterilizing. In one embodiment, as shown in FIG. 2C, the recessed portion 24 has an inner diameter 31 less than an outer diameter of the working end-site to be sterilized such that when a working end-site is received in the recessed portion 24 the inner walls 37 of the recessed portion conform to the outer surfaces of the working ends site. In some embodiments, the sterilizing element 20 may include a raised base portion 29 configured to project into and engage the surfaces of an inner lumen or septum, as described above.

Figure 3:
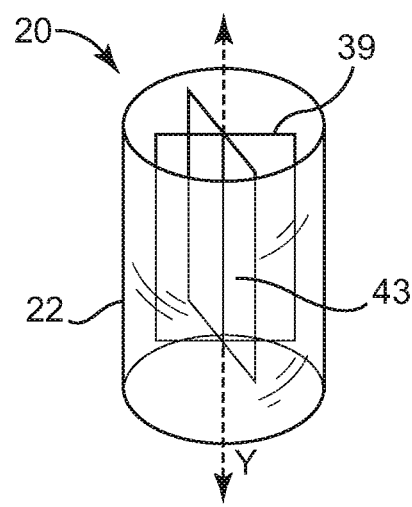
FIG. 3 is an isometric view of a sterilizing element according to another embodiment of the present invention.

FIG. 3 is an isometric view of a sterilizing element 20 according to another embodiment of the present invention. The sterilizing element 20 is made from a foam or sponge-like material and is die cut to conform to the surfaces of the working end-site to be sterilized. The die cut sterilizing element 20 can be cut in a number of configurations, such that it conforms to a variety of medical device connectors, components, and access ports. Additionally, according to some embodiments, the die cut sterilizing element 20 can be cut such that it is especially configured to accommodate a device having a lumen or septum. For example, the die cut sterilizing element 20 may be cut such that it is configured to project into and engage the inner surfaces of the a medical device having an inner lumen and/or a septum. In one embodiment, as shown in FIG. 3, the sterilizing element 20 includes an absorbent foam piece 22 that is die-cut to include at least one slit 39 formed along a longitudinal axis Y of the element 20 such that when a working end-site is depressed into the sterilizing element 20, the slit 39 opens to receive the working end-site therein. The slit 39 includes side walls 43 configured to conform to the surfaces of the working end-site to be sterilized.

Figure 4:
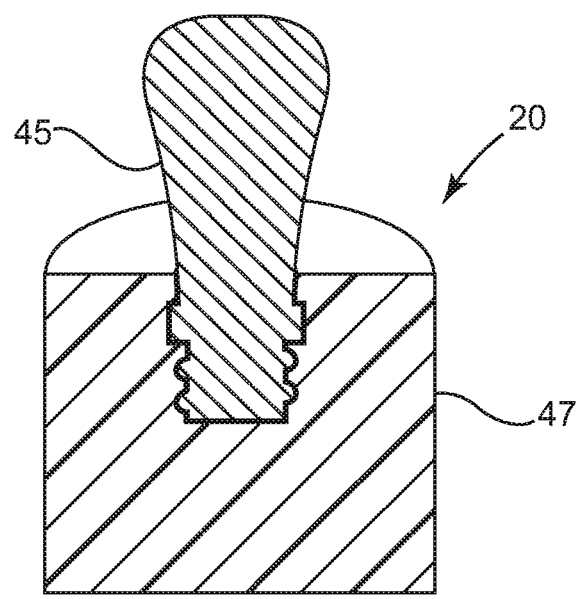
FIG. 4 is a cross-sectional view of a contoured sterilizing element engaged with a thread luer connector.

FIG. 4 is a cross-sectional view of a sterilizing element 20, according to yet another embodiment of the present invention, including a working end-site 45 of a device to be sterilized received therein. As shown in FIG. 4, the sterilizing element 20 includes an absorbent, resilient article 47. In one embodiment, the absorbent resilient article 47 is fabricated from a viscoelastic foam (e.g. viscoelastic polyurethane foam). The absorbent, resilient article 47 has sufficient resiliency such that when the working end-site 45 is pressed into the resilient article 47, the resilient article 47 depresses to receive the working end-site 45 to a depth sufficient for the effective wiping and sterilization of the working end-site 45. Additionally, when the working end-site 45 is pressed into the resilient article 47 to a sufficient depth, the depressed resilient article 47 conforms to the outer surfaces of the working end-site 45.

The sterilizing element 20, according to the various embodiments, described above may be formed using a variety of techniques. According to one embodiment, the sterilizing element 20 may be heat-set, molded, pressure-molded, injection-molded, cored, laser, and/or die cut. Other techniques known to those of skill in the art for forming and shaping foam may also be used.

Figure 5A:
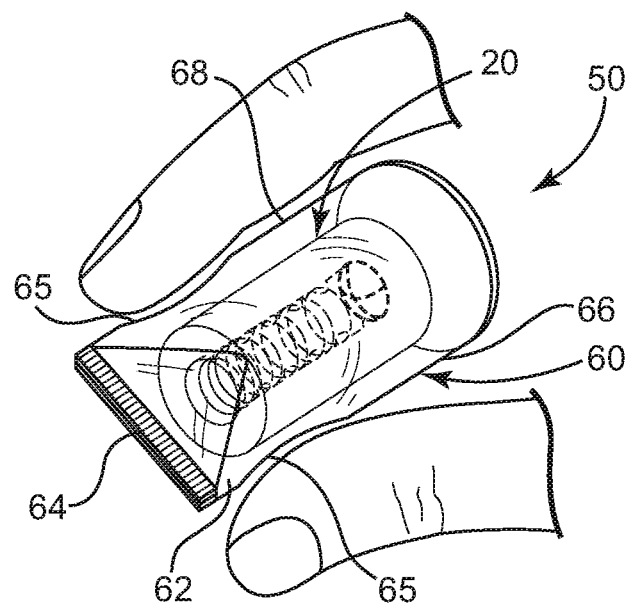
FIGS. 5A and 5B are isometric views of a sterilizing device according to one embodiment of the present invention.
Figure 5B:
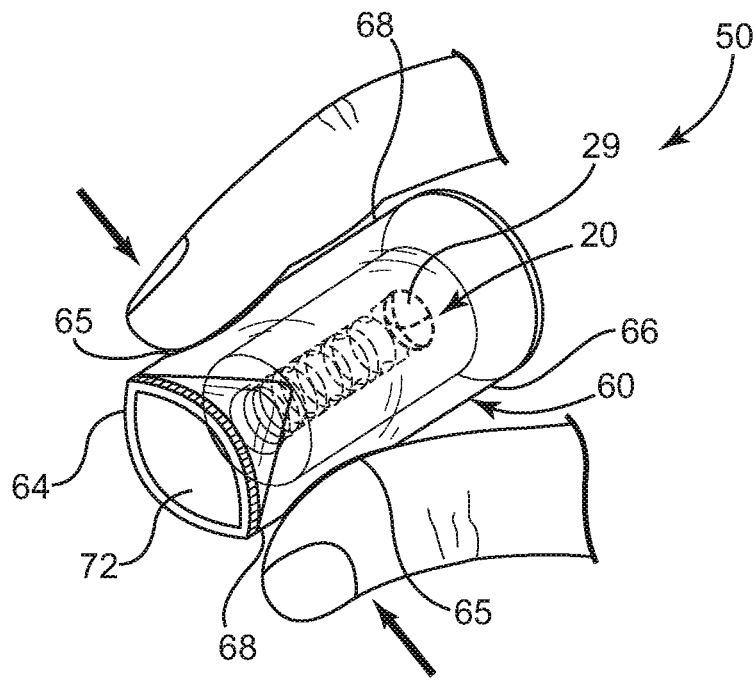

FIGS. 5A and 5B are isometric views of a sterilizing device 50 according to various embodiments of the present invention. As shown in FIGS. 5A and 5B, the sterilizing device 50 includes a sterilizing element 20, such as described above, according to the various embodiments, contained within a housing 60. According to some embodiments, the sterilizing element 20 is contained within the housing 60 such that the housing 60 provides a barrier to direct contact with the sterilizing element 20 when the sterilizing element 20 is in use, and serves as a tool for mechanically manipulating the sterilizing element 20. According to various embodiments, as will be described in further detail below, the housing 60 can include a top or lid to seal and protect the pre-moistened sterilizing element from drying out within the housing until it is ready for use.

The sterilizing element 20 is secured within the housing 60 to prevent dislodgement of the sterilizing element 20 from the working end-site of the device being sterilized. The sterilizing element 20 should be sufficiently secured within the housing 60 such that it can withstand vigorous wiping of an end-site. The sterilizing element 20 can be secured within the housing by various methods including, but not limited to, the following: ultrasonic welding, inward indentations of the walls, internal molded ribs or points, adhesives, frictional engagement, as well as the sterilizing element's own outward expanding radial force to hold it in place within the housing.

According to other embodiments, the sterilizing element 20 may be removed from the housing/packaging for attachment to and sterilizing of the end-site, as well as be directly held by and in the hand of the user to sterilize the end-site. The sterilizing element 20 has an inclusive layer of anti-pathogenic which to sterilize both the working end-site and the user's fingers. Alternatively, the contoured sterilizing element 20 may be left in place within the housing and the whole device can be left on the end-site for the purpose of protecting the site's sterility until such time the device is removed so that the site end can be used.

According to various embodiments, the housing 60 is small and ergonomically shaped so as to be easily held within the fingers of one hand of the user. In certain embodiments, the housing 60 is configured to be opened single handedly using the fingers on one hand. Additionally, the housing 60 can have a general shape such as an hourglass or flared shape that guides the placement of a user's fingers. According to other embodiments, the housing 60 can include one or more fingers locating features 65 formed with sidewalls 66 and 68 of the housing 60 to guide a user's placement of their fingers when using the device 50. The finger locating features 65 may also facilitate gripping and handling of the device by the user. According to various embodiments, the finger locating features 65 can include but are not limited to be dimples, bumps, grip marks, and other features useful for locating a user's fingers. As shown in FIGS. 5A and 5B the finger locating features 65 include recesses formed in the sidewalls 66 and 68 of the housing 60. According to some embodiments, the housing 60 can be opened using the fingers on a single hand.

The housing 60 is sized to receive the working end-site of a medical connection inserted therein. The medical device or working end-site is inserted into the housing to access the sterilizing element 20 contained therein. According to one embodiment, the housing 60 is configured such that the working end-site can be inserted to a depth of approximately 5 mm. In other embodiments, the housing 60 is configured such that the working end-site can be inserted into the housing 60 by a depth of about 3 mm to about 5 mm. In yet another embodiment, the working end-site may be inserted into the housing by a depth of about 4 mm.

The housing 60 can be made from a variety of materials. According to some embodiments, the housing 60 is made from a plastic, laminated paper/foil combination, or other semi-rigid material or semi-flexible material. As shown in FIG. 5A, a top portion 62 of the housing 60 can be pinched closed to form a seal 64. The seal 64 may be formed using ultrasonic welding, heat thinning and/or a liquid impermeable polyolefin film forming a combination molded seam and parting seal. As shown in FIG. 5B, the user squeezes the sidewalls 66 and 68 of the housing 60 inward with the fingers of one hand such that the seal 64 formed along the top portion 62 opens to form opening 72. The opening 72 is sized to receive the working end-site of a connection device or other medical device therein. In some embodiments, the squeezing action causes an audible "popping sound" as the seal 64 is forced open. Opening the seal 64 exposes the sterilizing element 20 secured within the housing 60 and allows for receipt therein of the working end-site of the connection device or other medical device to be sterilized.

Figure 6:
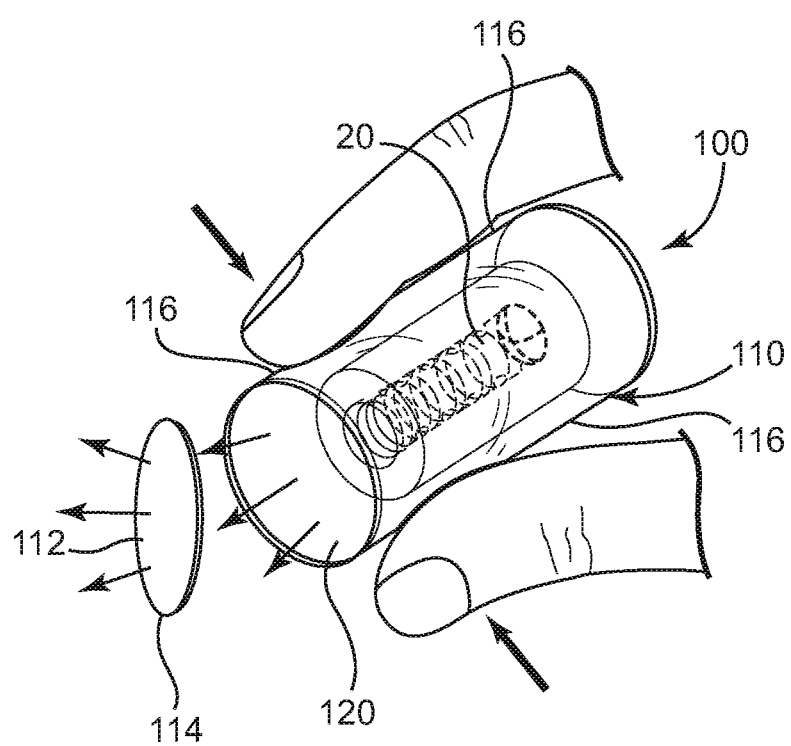
FIG. 6 is an isometric view of a sterilizing device according to another embodiment of the present invention.

FIG. 6 is an isometric view of a sterilizing device 100 including a pre-moistened sterilizing element 20 contained within a housing 110 according to another embodiment of the present invention. The sterilizing element 20 can have any configuration according to the various embodiments, as described above. As shown in FIG. 6, the housing 110 shows a frangible top 112 that can be sealed onto the housing 110 utilizing a combined molded seam and parting seal 114. The top 112 is secured to the housing 110 such that when the user squeezes the sidewalls 116 of the housing 110 with the fingers of one hand, the seal along the top 114 releases due to an increase in internal pneumatic pressure causing the top 112 to pop off and detach from the housing 110 to create an opening 120 facilitating access to the sterilizing element 20 contained inside.

Figure 7A:
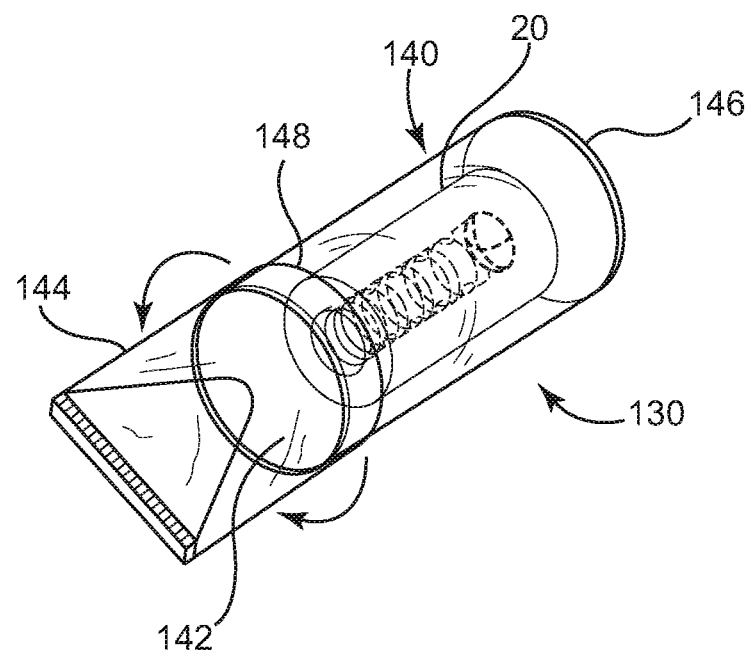
FIG. 7A is an isometric view of a sterilizing device including a housing having a removable cover according to still another embodiment of the present invention.
Figure 7B:
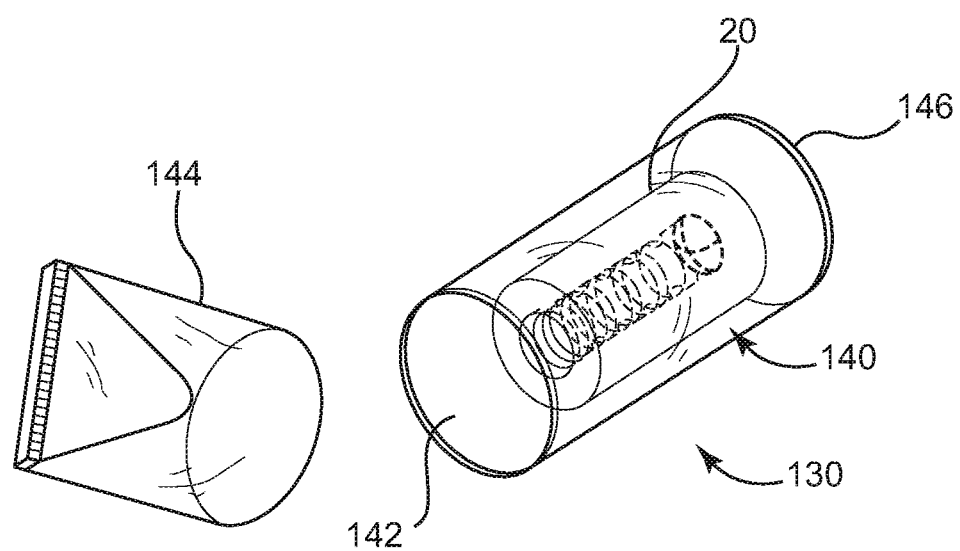
FIG. 7B is an isometric view of the sterilizing device shown in FIG. 7A, wherein the housing cover is removed.

FIGS. 7A and 7B are isometric views of a sterilizing device 130 according to another embodiment of the present invention. The sterilizing device 130 includes a pre-moistened sterilizing element 20 contained within a housing 140 having an opening 142, sized to receive the working end-site of a medical device. The sterilizing element 20 can have any configuration according to the various embodiments, as described above. The housing 140 includes a removable cover 144. As shown in FIG. 7A, the removable cover 144 can be secured to the housing 140 via a circumferential frangible tear line 148. As shown in FIG. 7B, the cover 144 can be removed using a twisting and pulling motion to detach the cover 144 from the housing 140 via the tear line 148. In some embodiments, the cover 144 and the body 140 can be made of plastic, mylar, foil, laminated foil, or other flexible material. In other embodiments, the cover 144 can be made of a semi-flexible or semi-rigid material.

Figure 8:
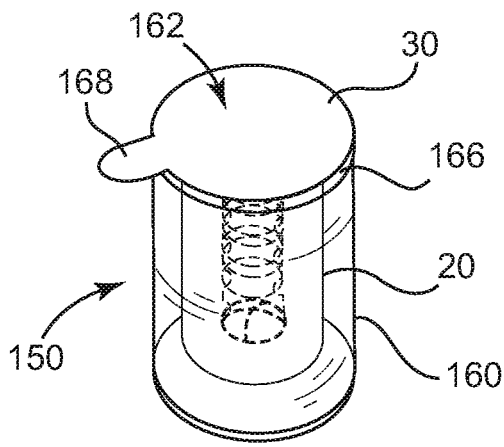
FIG. 8 is an isometric view of a sterilizing device including a housing having a removable lid provided in accordance with an embodiment of the present invention.
Figure 9:
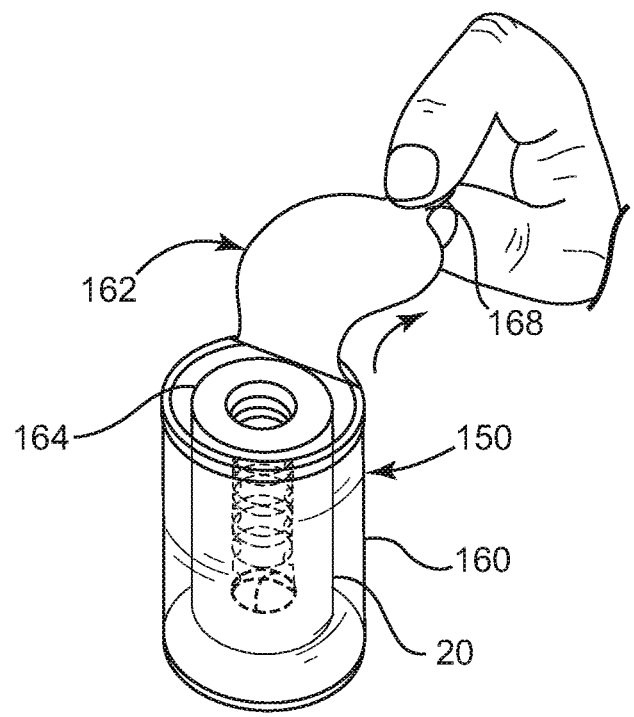
FIG. 9 is an isometric view of the sterilizing device shown in FIG. 8, wherein the lid is removed.

FIGS. 8 and 9 are isometric views of a sterilizing device 150 including a pre-moistened sterilizing element 20 contained within a housing 160 having a removable cover 162 according to another embodiment of the present invention. The sterilizing element 20 can have any configuration according to the various embodiments, as described above. According to one embodiment, the removable cover 162 is a peel-away lid. As shown best shown in FIG. 8, the cover 162 is secured over the top opening 164 of the housing 160 such that it seals the pre-moistened sterilizing element 20 within. The cover 162 includes a circumferential tear line 166 for facilitating its removal. Additionally, the cover 162 can also include a tab or tether 168. According to one embodiment, as shown in FIG. 9, a user manually grasps the tab or tether 168 and pulls the cover 162 from the housing via the tear line 166 to reveal the opening 164 and grant access to the sterilizing element 20 contained within.

Figure 10:
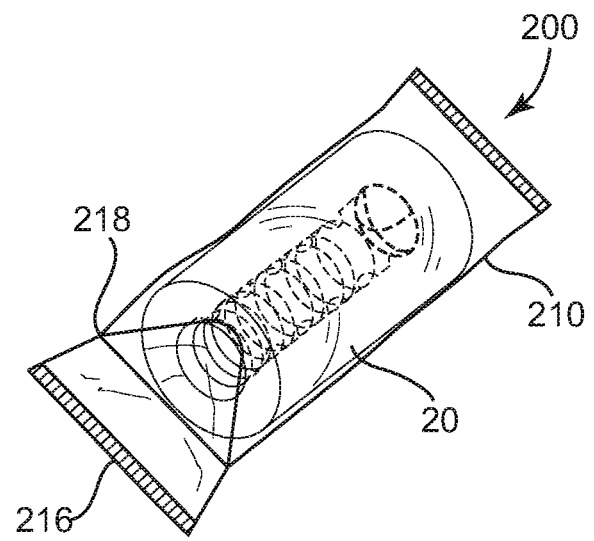
FIG. 10 is an isometric view of a sterilizing device including a housing having a tear off end provided in accordance with an embodiment of the present invention.
Figure 11:
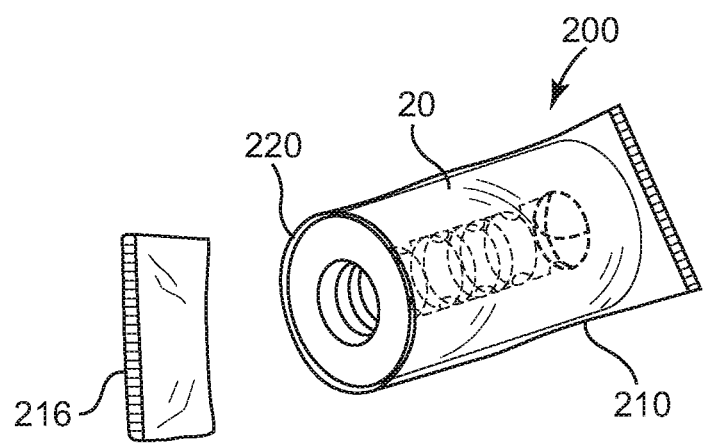
FIG. 11 is an isometric view of the sterilizing device shown in FIG. 10, wherein the end is removed.

FIGS. 10 and 11 are isometric views of a sterilizing device 200 including a pre-moistened sterilizing element 20 contained within a flexible envelope housing 210 according to yet another embodiment of the present invention. The sterilizing element 20 can have any configuration according to the various embodiments, as described above. The flexible envelope housing 210 may be formed from plastic, mylar, foil, laminated, or other flexible material. According to a further embodiment, the flexible envelope housing 210 may include a foil lining to further maintain the moisture level of the sterilizing element contained within. As shown in FIGS. 10 and 11, the flexible envelope housing 210 includes a removable protective cover 216. The removable protective cover 216 can include a line of perforations or weakness 218 configured to facilitate removal of the protective cover 216 from the housing 210. The removable protective cover 216 may be removed from the housing by tearing or cutting along the line 218. FIG. 11 shows the protective cover 216 removed from the housing 210 to create an opening 220 facilitating access to the sterilizing element 20 contained within.

Figure 12:
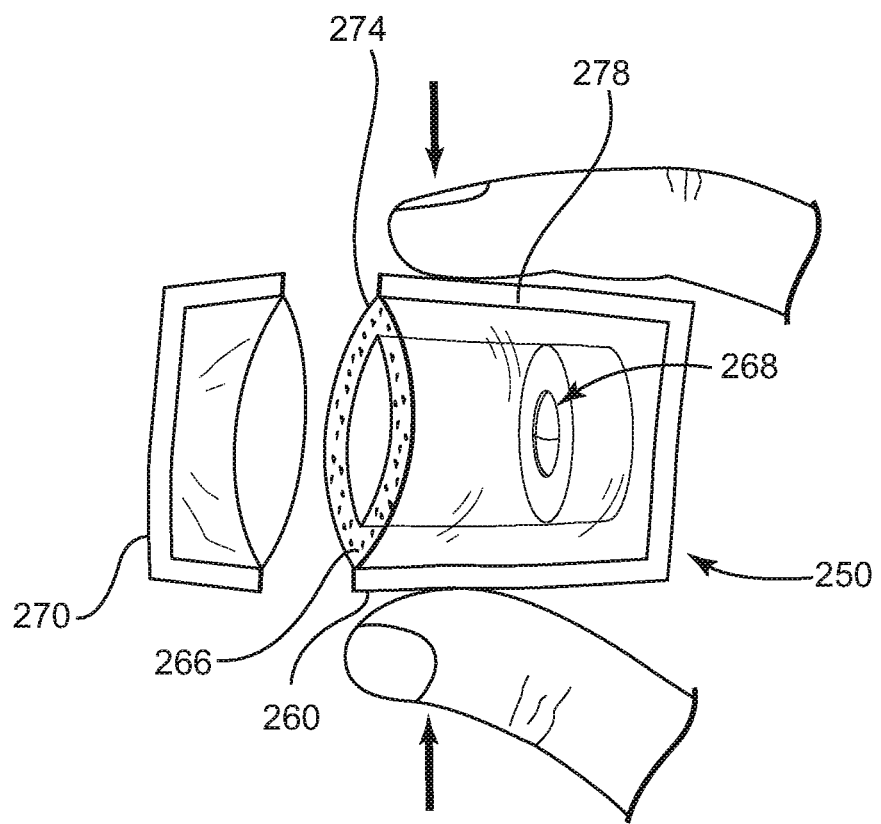
FIG. 12 is an isometric view of a sterilizing device according to yet another embodiment of the present invention.

FIG. 12 is an isometric view of sterilizing device 250 according to another embodiment of the present invention. The sterilizing device 250 includes a flexible envelope housing 260 including an inner lining 266 and a removable protective cover 270. In some embodiments, the removable protective cover 270 can be removed from the housing 260 by tearing or cutting along a perforation line or other similar line of weakness. The protective cover 270 is shown removed from the housing 260 in FIG. 12.

The inner lining 266 can be made of a particulate free absorbent foam or sponge-like material. The absorbent foam or sponge-like material is pre-moistened with an anti-pathogenic agent, as previously described above and lines the inner walls of the envelope housing 260. The inner foam lining 266 is contoured and can include a plurality of raised ridges, ribs or threads configured to engage the threads, sides, and/or edges on the working end-site. Additionally, as shown in FIG. 12, the inner foam lining 266 includes raised base 268 configured to project into and to engage the inner luer lumen and/or septum of a needleless connector or port end. Additionally, according to a further embodiment, the inner lining 266 can include a reinforced oval rim 274. The reinforced oval rim 274 is adapted to flex from a closed position to an open position by squeezing the sides 278 of the flexible envelope housing 260 upon removal of the protective cover 270. The rim 274 is flexed open to facilitate the reception of a working end-site of a device to be sterilized within the inner lining 266 of the envelope 260.

Figure 13A:
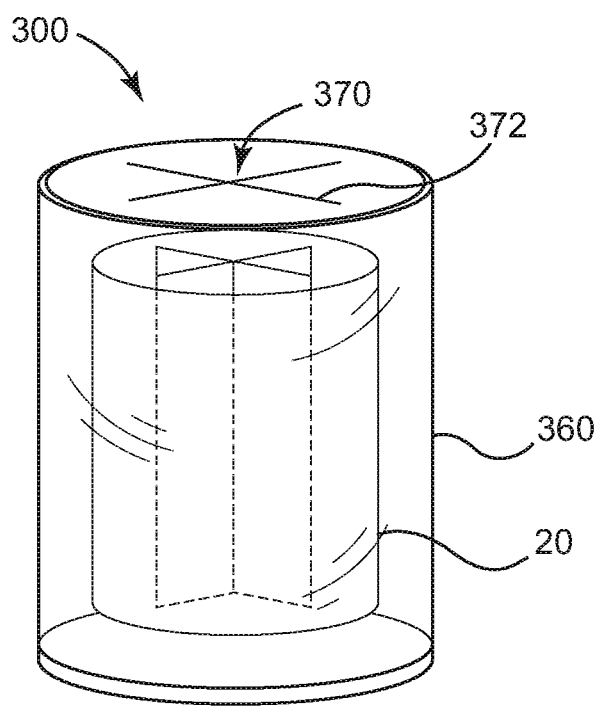
FIG. 13A is an isometric view of a sterilizing device including a frangible top according to an embodiment of the present invention.
Figure 13B:
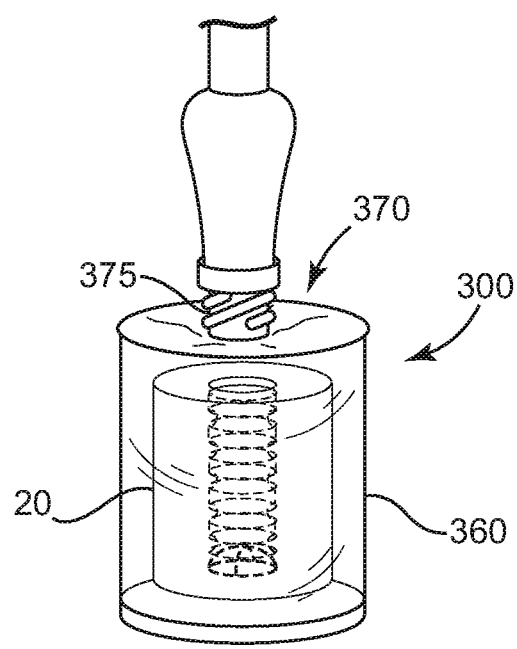
FIG. 13B is an isometric view of a working end-site forcibly engaged through the frangible top of a sterilizing device.

FIG. 13A is an isometric view of a sterilizing device 300 including a sterilizing element 20 contained within a generally cylindrical housing 360. The sterilizing element 20 can have any configuration according to the various embodiments, as described above. According to one embodiment, the housing 360 includes a frangible lid 370. The lid 370 seals the pre-moistened sterilizing element 20 and maintains a moisture rich environment inside the housing 360. According to various embodiments, the frangible lid 370 can be made of plastic, mylar, foil, laminated foil, laminate, or other similar material. In some embodiments, the frangible lid may include score-marks 372 to facilitate breaking of the frangible lid 370. The frangible lid 370 should be of sufficient thickness and frangibility, that the working end-site 375 (as shown in FIG. 13B) of a device to be sterilized, can penetrate the lid by forcibly engaging the working end-site through the pre-scored lid to access the sterilizing element 20 contained within the housing 360. FIG. 13B shows a working end-site of a device to be sterilized forcibly engaged through the frangible top 370 of the sterilizing device 300.

In some embodiments, the housing 360 is sized to facilitate prolapse of the frangible lid 370 into the housing 360. For example, as the working end-site 375 is being forcibly engaged through the frangible lid 370, the lid material pushes inward and down into the housing 360 such that the working end-site 375 can access and engage the sterilizing element 20 contained within the housing 360. In some embodiments, the working end-site 375 can be left engaged with the sterilizing element 20 contained within the housing 360 until the end-site 375 is ready for use. Together with the lid 370, the housing 360 and the sterilizing element 20 have sufficient integrity and durability such that the device 300 resists removal of the end-site 375 from the device 300 thus allowing the device 300 to be left engaged with the end-site 375 without the potential for inadvertent disengagement from the device 300. According to one embodiment, the housing 360 provides a depth of less than about 10 mm to facilitate prolapse of the lid 370 into the housing 360. In another embodiment, the housing 360 provides a depth of about 5 mm to about 10 mm, of about 3 to about 5 mm, and/or about 4 mm to facilitate prolapse of the lid 370 into the housing 360.

Figure 14:
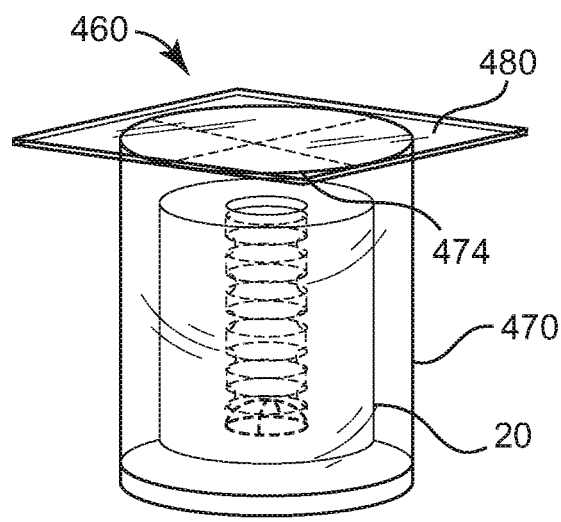
FIG. 14 is an isometric view of a sterilizing device including a protective cover according to other embodiments of the present invention.

FIG. 14 shows a sterilizing device 460 according to a further embodiment of the present invention. As shown in FIG. 14, the sterilizing device 460 includes a pre-moistened sterilizing element 20 according to the various embodiments as described above, contained within a housing 470 having a lid 474 and an additional debris protective covering 480. The lid 474 is secured to the top of the housing 470 to seal the pre-moistened sterilizing element 20 within the housing. According to one embodiment, as previously described above, the lid 474 is a foil or plastic frangible lid and may be pre-scored to include score-marks. Additionally, the lid 474 is of sufficient thickness and frangibility such that a working end-site of a device to be sterilized can be forced through the lid 474 to access the sterilizing element 20 contained within the housing 470.

The debris protective covering 480 is positioned adjacent and secured to the lid 474. The debris protective covering assists in keeping the device lid 474 free of debris until the device is ready for use. The debris protective covering 480 extends outward beyond an outer diameter of the housing 470. This configuration helps to stabilize the device 460 and may prevent it from rolling when the device 460 is placed on its side. Additionally, the configuration may provide a wider, sturdier base for the device 460, if the device is placed top-side-down on a flat surface. The debris protective covering 480, as shown in FIG. 14, can be used in conjunction within a variety of housing configurations, such as those described above.

FIG. 15 is an isometric view of a dual sided sterilizing device 500 according to yet another embodiment of the present invention. As shown in FIG. 15 the dual sided sterilizing device 500 includes an elongated ergonomic housing 510, having a first end 512 including a first opening 514 and a second end 516 including a second opening 518. At least one sterilizing element 520 is located within the housing 510 and can be accessed through either the first or second opening 514 or 518.

According to one embodiment, the housing 510 includes a seal or lid 530 located over each of the first and second openings 514 and 518. The lid or seal 530 can have any one of the configurations as described above. According to one embodiment, as shown in FIG. 15, the lid 530 can be a pre-scored lid. According to further embodiments each of the first and second ends 512 and 516 can include a plastic, foil, or laminated lid 530 that is of sufficient thickness and frangibility that a working end-site of a device to be sterilized can be forced through the lid to gain access to the sterilizing element contained inside. In some embodiments, a protective covering, such as described above with reference to FIG. 14, may be secured to the lid 530.

According to various embodiments, the dual sterilizing element 520 contained within the housing 510 can be made from a non-woven, particulate free absorbent foam, or sponge-like material. The absorbent foam or sponge-like material is pre-moistened with an anti-pathogenic agent including any one of an antiseptic, disinfectant, microbiocidal, or combinations thereof to kill pathogens on the surfaces of the device. Additionally, the sterilizing element 520 is contoured and shaped so that it "form-fits" over the working end-site of a luer compatible connector, device, and/or needle access port for efficient wiping and sterilizing. According to one embodiment, the sterilizing element 520 can extend continuously from the first end 512 to the second end 516 throughout the entire housing length 510. According to another embodiment, described in further detail below, the sterilizing element 520 can include two separate portions contained within the housing 510.

Like the housing 510, the dual sterilizing element 500 includes a first end 522 and a second end 524. Each end 522 and 524 can be shaped to fit to the various male, female (inner lumen), slip luer, septum, port, or threaded configurations of a working end-site to be sterilized, and apply an inclusive layer of an anti-pathogenic agent to sterilize and wipe debris from the site while using a wiping and twisting motion. According to one embodiment, each end 522 and 524 can have the same contouring. According to another embodiment, the first end 522 and the second end 524 can have different contouring. For example, the first end 522 can be contoured such that it contacts and engages the surfaces of a male connection component (e.g. male luer lock or a slip luer) and the second end 524 can be contoured such that it projects into and engages the surfaces of various female (inner lumens) and/or septums (e.g. a needleless injection port).

According to further embodiments, each of the first and second ends 514 and 518 can include a label (not shown) located on an outer surface of the housing 510. The label can be embossed or printed with differentiating numbers, letters, or symbols to assist the clinician in identifying which end of the housing they are using. Using labels to identify the working ends 514 and 518 is useful, for example, when the first and second ends 522 and 524 of the sterilizing element 520 differ so as to be used to clean and sterilize different medical devices. Additionally, labels to identify the working ends 514 and 518 of the device 500 are also useful when the anti-pathogenic agents on the first and second ends 522 and 524 of the sterilizing element 520 differ such that the anti-pathogenic agent can be selected depending on the material to be sterilized. In certain embodiments, when the sterilizing device 500 is left engaged with the working end-site after it has been cleaned and sterilized, a label can be used to signify to the user or users that the connection has been sterilized and is ready for use.

FIG. 16 is a schematic view of the dual sided sterilizing device 500 shown in FIG. 15 according to another embodiment of the present invention. According to one embodiment, as shown in FIG. 16, a divider or partition 560 separates the device into two distinct portions 562 and 564. According to this embodiment, each of the portions 562 and 564 contain a separate sterilizing element 520a or 520b. The sterilizing elements 520a and 520b are secured to the divider in a back-to-back arrangement. The sterilizing elements 520a and 520b can have the same or different contour configurations. For example sterilizing element 520a can be configured to engage male luer connections and sterilizing element 520b can be configured to engage female luer connections and/or septums. Additionally, the sterilizing elements 520a and 520b can be pre-moistened with the same or different anti-pathogenic agent. According to yet another embodiment, the second sterilizing element 520b can be dry and can be used to dry the working end-site after the working end-site has been cleaned and sterilized using the first pre-moistened sterilizing element 520a. The second portion 564 containing the dry sterilizing element can be left engaged with the working end-site until the end-site is ready for use.

Figure 17:
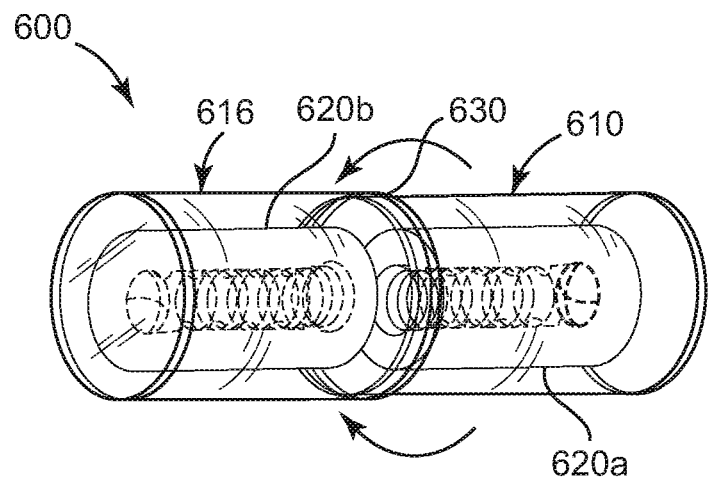
FIGS. 17 and 18 are isometric views of a combined sterilizing device according to yet another embodiment of the present invention.
Figure 18:
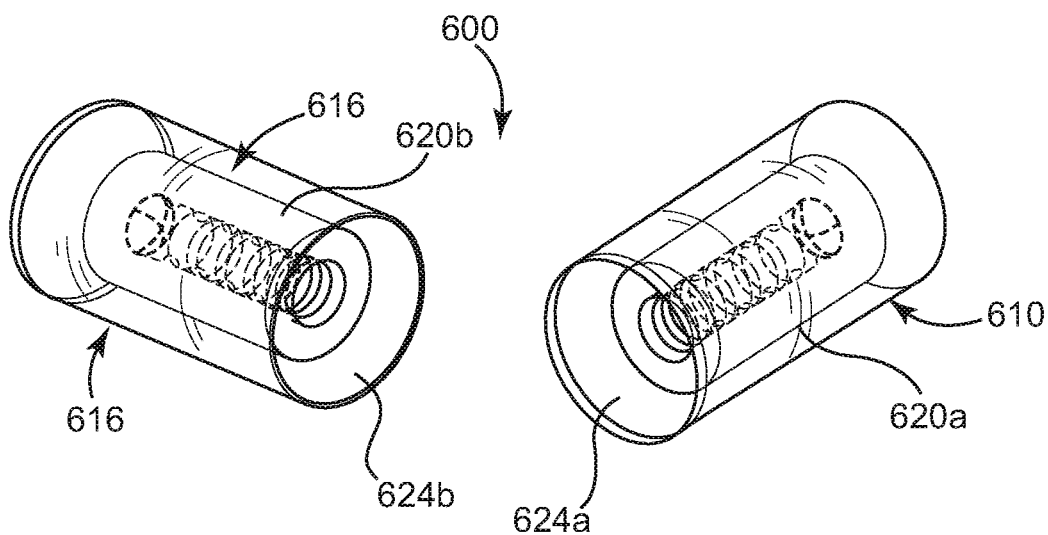

FIGS. 17 and 18 show a combined sterilizing device 600 according to yet another embodiment of the present invention. As shown in FIGS. 17 and 18, the sterilizing device 600 includes a housing 610 and a cover 616. Each of the housing 610 and the cover 616 contain a sterilizing element 620a and 620b, respectively. The sterilizing elements 620a and 620b can have any one of the configurations according to the various embodiments described above. The cover 616 is coupled to the housing 610 via a frangible seal 630, as shown in FIG. 17. The cover 616 can be separated from the housing 610 by a twisting and pulling motion to gain access to the sterilizing elements 620a and 620b through separate openings 624a and 624b located in the housing 610 and the cover 616, respectively. The housing and cover portions 610 and 616 of the device 600 can be used separately to clean and sterilize the working end-sites of one or more devices to be sterilized. According to further embodiments, the sterilizing elements 620a and 620b contained within the housing 610 and cover 616, respectively, can have the same or different configurations. Additionally, the sterilizing elements 620a and 620b can be pre-moistened with the same or different anti-pathogenic agent. For example, the sterilizing element 620a located within the housing 610 can be contoured so as to contact and engage the surfaces of male devices and can be pre-moistened with a first anti-pathogenic agent, and the sterilizing element 620b located within the cover 616 can be contoured so as to contact and engage the inner surfaces and a device having a lumen and/or septum and can be pre-moistened with the same or a second anti-pathogenic agent. According to other embodiments, the first sterilizing element 620a can be pre-moistened with an anti-pathogenic agent and is used to clean and sterilize the working end-site. The second sterilizing element 620b can be dry and used to dry the working end-site after it has been cleaned using the first sterilizing element 620a. The cover 616 including the dry sterilizing element 620b may be left engaged with the working end-site until the site is ready for use.

Figure 19A:
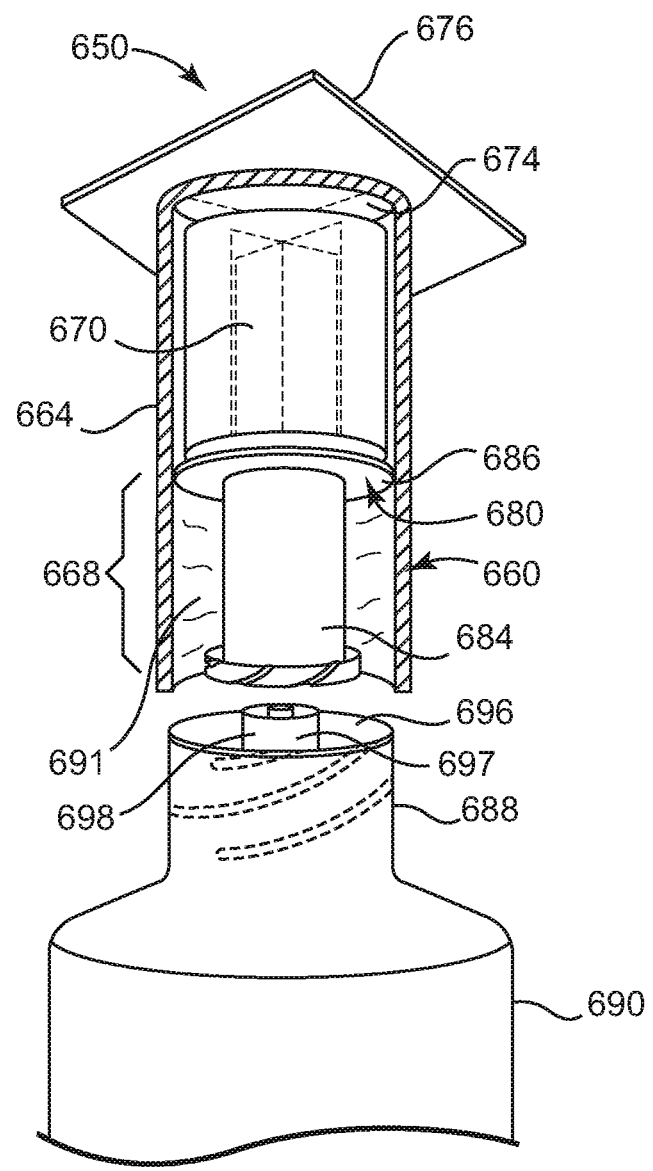
FIGS. 19A and B are partial cut-away views of a sterilizing device configured to be attachable to a syringe according to yet other embodiments of the present invention.

FIGS. 19A and B are partial cut-away views of a sterilizing device 650 according to still other embodiments of the present invention. As shown in both FIGS. 19A and 19B, the sterilizing device 650 includes an elongated housing 660 having an upper portion 664 and a lower portion 668. A pre-moistened sterilizing element 670, according to any one of the various embodiments as described above, is sealed within the upper portion 664 of the housing 660 by a frangible top 674. According to one embodiment, a protective cover 676, such as previously described above, can be provided over the frangible top 674. In one embodiment, as shown in FIG. 19A, the lower portion 668 of housing 660 includes a divider or partition 680 and a female luer 684 attached to an underside 686 of the divider 680. The female luer 684 is configured such that it can be secured onto a working end 688, for example, of a male luer lock syringe 690 or slip luer style syringe. The lower portion 668 of the housing 660 covers the syringe end 688 when the female luer 684 is coupled to the syringe end 688.

Figure 19B:
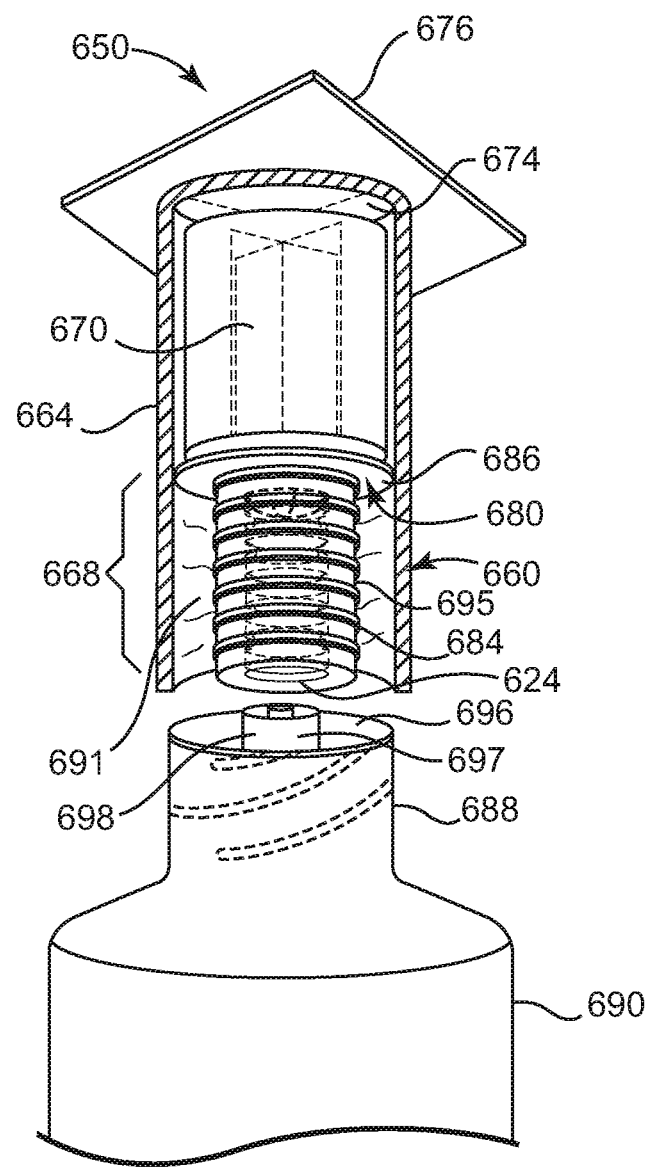

According to another embodiment, as shown in FIG. 19B, the lower portion 668 of the housing provides an inner surface to be retained onto the outside surface of the syringe 688. The lower portion 668 includes an inner lining 691 that has "grippable" or a textured surface that would allow the clinician to rotate the attached sterilizing device 650 either clockwise or counter clockwise in a manner to sterilize the end-site of the medical device while attached to the syringe end 668. The inner lining 691, along with a textured partition 680, provides a high-friction contact surface to prevent slippage of the housing 660 and particularly the lower portion 668 of the device 650 coupled to the syringe end 688. The grippable inner lining 691 having a textured surface provides an additional method of securing the sterilizing device 650 to the outer-housing of the syringe 690, particularly when the user is swabbing an end-site in a counter-clockwise direction where a partition 680 containing a female luer is coupled to the male luer lock on a syringe-end 688, such as shown in FIG. 19A, as it is generally recognized that a female luer coupled to a male luer lock are mechanically suitable for a clockwise rotation, but not a counter clockwise, rotation. Additionally, the lining 691 provides the additional high-friction for the user to turn the syringe 690 in a counter-clockwise direction to minimize the risk of the syringe 690 and sterilizing device 650 separating during a vigorous bi-directional (clockwise or counter clockwise) cleaning of the end-site. Further, in another embodiment, the lower portion 668 of the sterilizing device 650 does not include a female luer, and the inner lining 691, in conjunction with having a textured/lined partition 680, provides the necessary grip alone to the syringe's outer-housing/shroud (i.e. male luer lock syringe) for a bi-directional cleaning.

Additionally, in other embodiments, as shown in FIG. 19B the lower portion 668 can also include a sterilizing element 695 configured such that the inner cavity 624 of the sterilizing element 695 as well as the exterior 684 of the sterilizing element 695 would provide an alternative method for gripping the inner surface 696 of the male luer lock syringe end 688 and/or in conjunction with the inner lining 691 and/or the outer surface 697 of the slip luer portion 698 of the syringe 690. Together or in part, the lower portion 668 inner lining 691 and/or the sterilizing element 695 would provide a friction fit such that the clinician can rotate in either a clockwise or counter clockwise direction to sterilizing the medical device end-site. with the sterilizing element 695. Thus, the device 650, as described above according to the various embodiments, serves as both a sterilizing device and as an end-cap to keep the syringe end sterile and free from debris until the syringe is ready for use. After the working end-site of the medical connector has been wiped free of debris and is sterilized using the device 650, the housing 660 and lower portion 668, including the female luer 684 and/or sterilizing element 695, can be disengaged from the male end 688 of the syringe 690, and the contents of the syringe 690 can then be injected into the working end-site of the sterilized medical connector.

Figure 20:
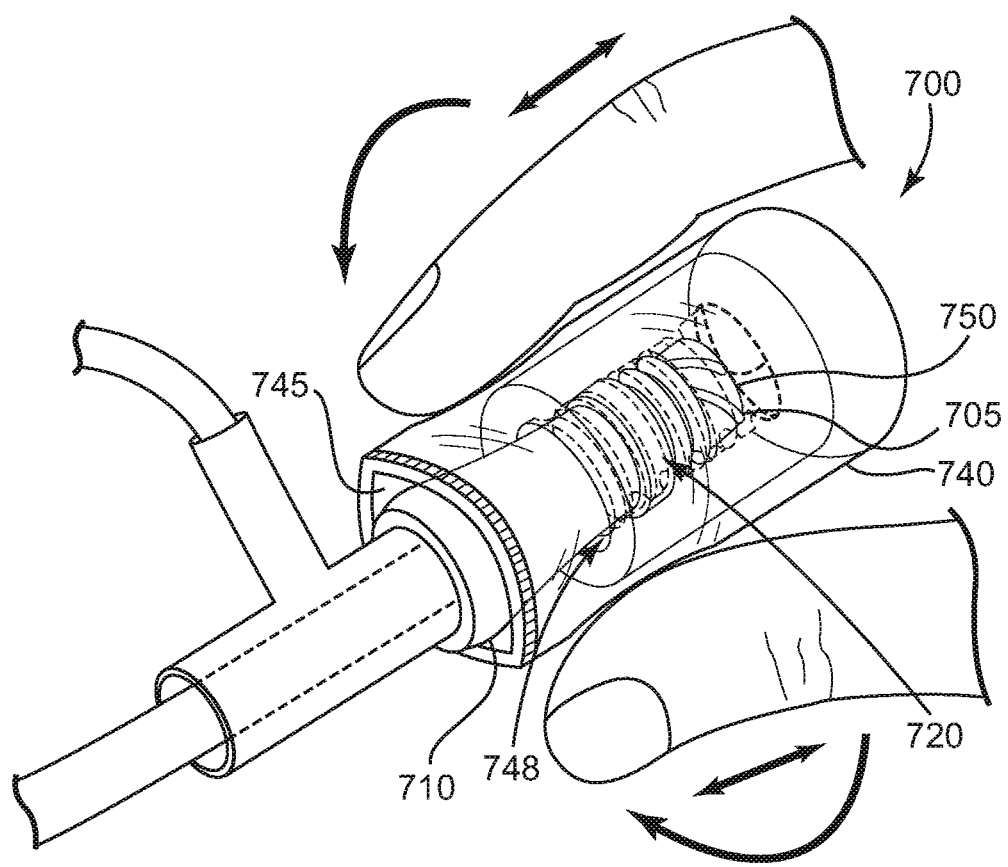
FIG. 20 is a perspective view of a sterilizing device including a sterilizing element provided in accordance with various embodiments of the present invention, in use.

FIG. 20 shows a sterilizing device 700 according to the various embodiments of the present invention, as described above, used to sterilize the working end-site 705 of a medical device 710. The sterilizing device 700 is intended for a single application and should be disposed of in the appropriate waste receptacle. The sterilizing device 700 includes a contoured sterilizing element 720 pre-moistened with an anti-pathogenic agent contained within a housing 740. In order to use the sterilizing device 700, the protective cover (if present) is first removed. Next, the housing 740 is opened to facilitate access to the sterilizing element. According to some embodiments, the housing 740 can be opened by peeling away or removing a lid secured to the top of housing. In other embodiments, the housing 740 may be opened by the application of inward pressure on the housing side walls to either break a seal formed at the top of the housing 740 or to pop off a lid. In still other embodiments, a working end-site of a device to be sterilized can be forcibly engaged through a frangible pre-scored lid or foil/laminated top to gain access to the sterilizing element 720 contained within the housing 740.

Once the housing 740 has been opened, the working end-site 705 of the device to be sterilized 710 is then inserted through the opening 745 of the sterilizing device housing 740 to access the sterilizing element 720 contained within, as shown in FIG. 20. The end-site 705 is inserted into the recessed portion 748 of the sterilizing element 720, such that the sterilizing element 720 contours to the outer threads, edges, sides, and inner lumen surfaces of the medical connector end. As shown in FIG. 20, the sterilizing element 720 includes a recessed portion 748 configured to contour to the outer surfaces and threads of the end-site and a raised base portion 750 adapted to contact and engage the distal end including the distal tip of the working end-site 705 as well as the inner lumen of the medical connector, as described above.

Debris is cleared from and an inclusive layer of ant-pathogenic agent is applied to the end surfaces of the working end-site 705 with the contoured sterilizing element 720 using a wiping and/or twisting motion for sufficient amount of time so as to achieve a specific "kill of microbes." According to some embodiments, cleaning and sterilizing the working end-site 705 includes expelling the anti-pathogenic agent onto the working end-site 705. For example, in one embodiment, the working end-site 705 is compressed into the sterilizing element 720 to expel the anti-pathogenic agent from the element 720 and onto the working end-site 705. In another exemplary embodiment, the anti-pathogenic agent can be expelled onto the working end-site 705 by squeezing the sidewalls of the housing 740 to compress the sterilizing element 720 contained therein to expel the anti-pathogenic agent onto the working end-site 705. According to one embodiment, the cleaning time is less than about 30 seconds. According to another embodiment, the cleaning time ranges from about 20 to about 30 seconds; from about 15 to about 30 seconds; or from about 10 to about 30 seconds. In some embodiments, the sterilizing device 740 may be left engaged with the working end-site 710 until ready for use.

Once the working end-site 705 has been cleaned and sterilized for the appropriate amount of time, the working end-site then can be removed from the sterilizing element 720 and the housing 740, and allowed to air dry prior to connection of another compatible device or an injection made therein with a syringe. According to one embodiment, the drying rate after the anti-pathogenic agent has been applied to the working end-site is less than about 15 seconds. In other embodiments, the drying rate is less than about 10 seconds. In still other embodiments, the drying rate is less than about 7 seconds.

In other embodiments, a second end of the sterilizing device or an additional device including a dry element may be used to wipe dry the working end-site 705 after it has been cleaned and sterilized as described above. The second end or additional drying device may be left in place engaged within the working end-site until ready for use.

Figure 21A:
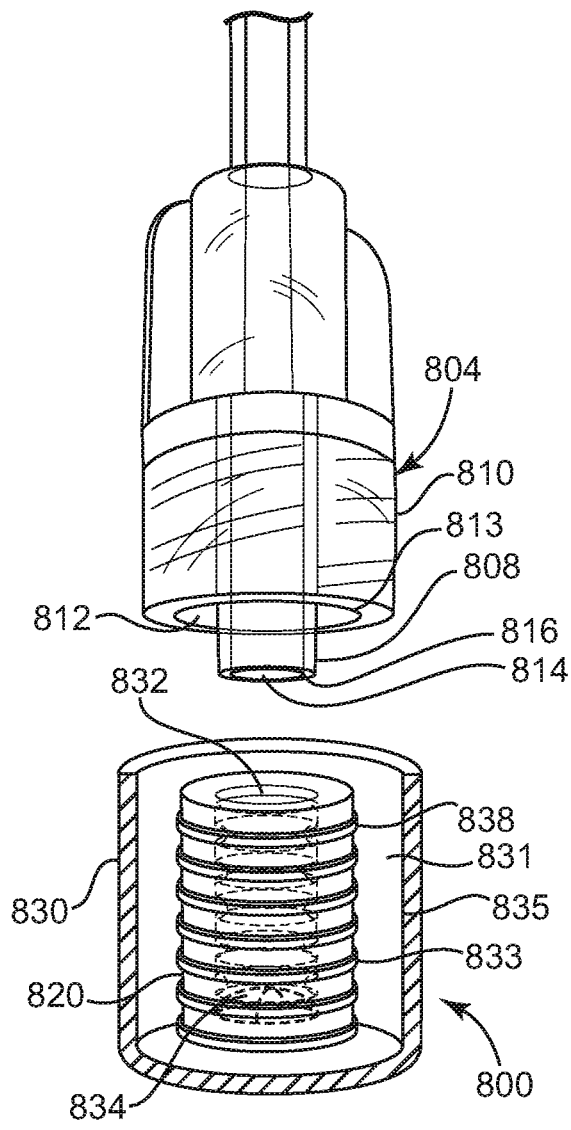
FIG. 21A is a partial cut-away view of a sterilizing device provided in accordance with various embodiments of the present invention and a male luer lock connector end.

FIG. 21A is a partial cut-away view of a sterilizing device 800 provided in accordance with various embodiments of the present invention and an exemplary connector end 804. As shown in FIG. 21A, the exemplary connector end 804 is a male luer lock connector including a male slip luer component 808 and a shroud 810 that covers and protects the slip luer component 808. An internal cavity 812 is defined between the shroud 810 and the slip luer component 808. The internal cavity 812 may include a plurality of internal threads provided on an inner wall or surface 813 of the shroud 810. The male slip luer component 808 includes a lumen 814 having an inner surface 816 and completes the fluid pathway common to male luer lock connectors.

According to various embodiments, the sterilizing device 800 includes a sterilizing element 820 contained within a housing 830. The sterilizing element 820 can have any one of the configurations according to the various embodiments described above. In one exemplary embodiment, the sterilizing element 820 includes an absorbent material pre-moistened with an anti-pathogenic agent. In certain embodiments, as shown in FIG. 21A. The housing 830 defines a cavity 831 between an outer surface 833 of the sterilizing element 820 and an inner wall 835 of the housing 830 to receive and couple with the male luer lock shroud 810. Additionally, the sterilizing element 820 includes a recessed portion 832 configured to receive and conform to the male slip luer component 808 (if present). Additionally, the sterilizing element 820 includes a raised base portion 834 configured to project into and engage an inner surface 816 of the slip luer lumen 814. Further, in certain embodiments, the outer surface 833 of the sterilizing element can be contoured to include, but not limited, ribs, threads, flanges or raised structures 838 and to contact all inner walls of the shroud 810 and to facilitate the wiping and sterilizing therein. The housing 830 can have a number of configurations, according to the various embodiments described above.

Figure 21B:
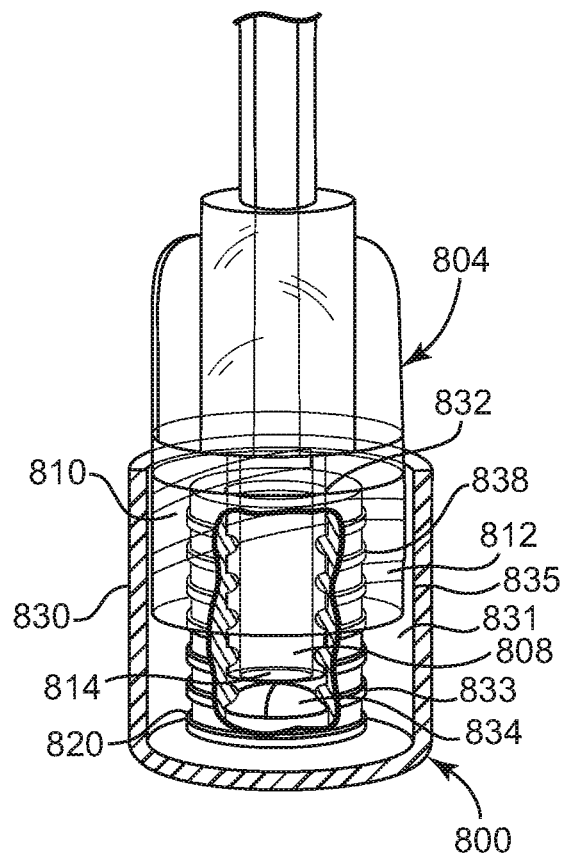
FIG. 21B is a partial cut-away view of the sterilizing device shown in FIG. 21A used to clean the male luer lock connector end.

FIG. 21B is a partial cut-away view of the sterilizing device 800 coupled with the male luer lock connector 804. In certain embodiments, as shown in FIG. 21B, the housing 830 is sized to fit over the shroud 810. The male slip luer component 808 (if present) is received and engaged in the recessed portion 832 of the sterilizing element. The sterilizing element 820, as shown in FIG. 21B, fills the internal cavity 812 defined by the shroud 810. Additionally, the shroud 810 fits sufficiently in housing cavity 831 between inner housing wall 835 and the outer wall 833 of the sterilizing element 820. The raised base portion 834 projects into and engages the inner surface 816 of the slip luer lumen 814. In some embodiments, the outer wall 833 of the sterilizing element 820 may include external surface features 838 configured to engage and contact any internal threads provided on the internal surfaces 813 of the shroud 810. Once the male luer connector 804 is engaged within the sterilizing element 820 contained within the housing 830, a wiping and/or twisting motion can be employed to wipe debris from and apply an inclusive layer of the anti-pathogenic agent to the inner and outer surfaces 812 of the male luer connector 804 including the inner surface 816 of the lumen 814. Once the male luer connector 804 has been effectively cleaned and sterilized, the sterilizing device 800 can be left on the end-site to protect its sterility until time of use and then disposed of in the appropriate waste receptacle. In certain embodiments, such as in the absence of a male connection component, the sterilizing element can be inserted into the cavity 831 defined by the shroud 810. Once the sterilizing element is engaged in the shroud, a wiping and/or twisting motion can be employed to clean and sterilize the surfaces of the medical device to be cleaned. The sterilizing device 820 can be left engaged in the shroud 810 until the device is ready for use.

Figure 22A:
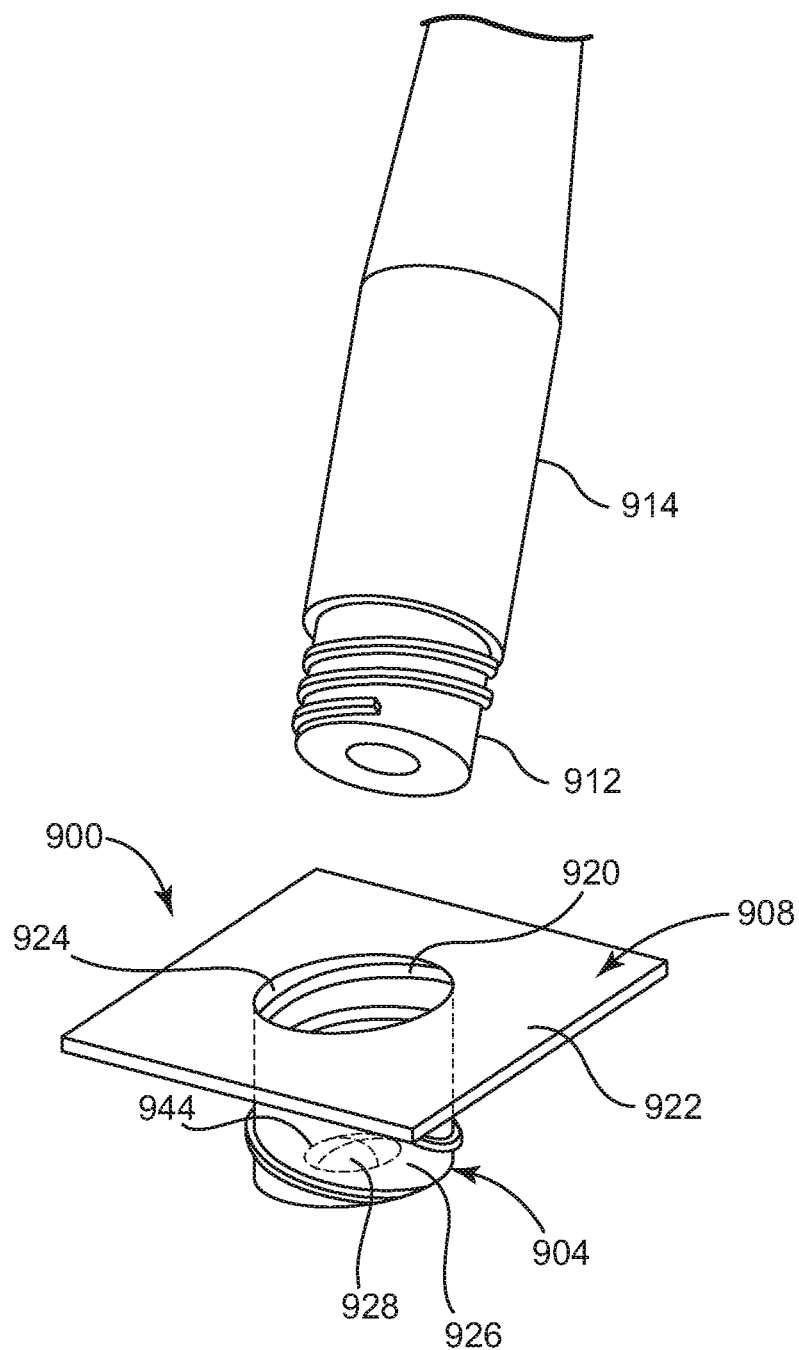
FIGS. 22A and 22B are isometric views of a contoured sterilizing tool according to still another embodiment of the present invention.
Figure 22B:
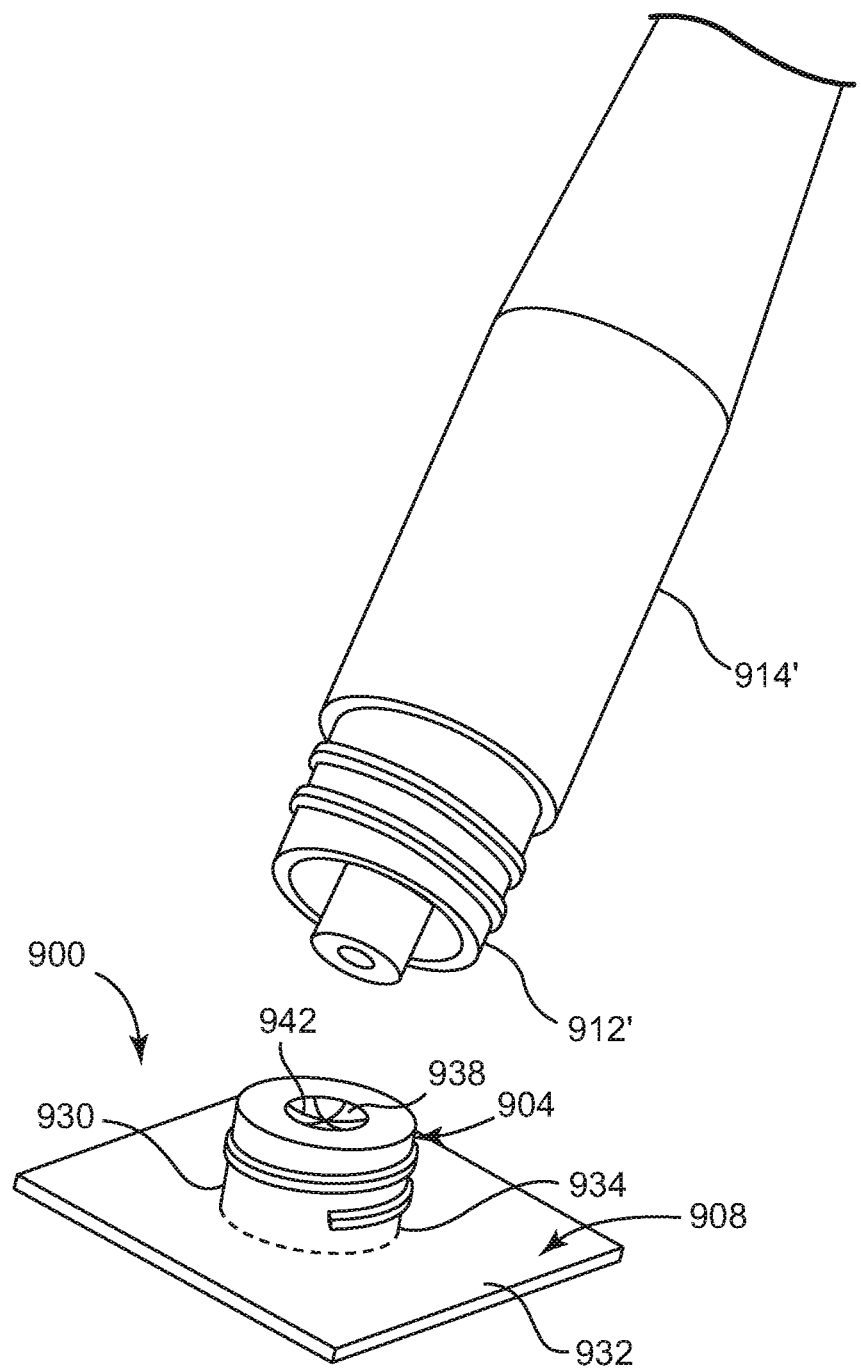

FIGS. 22A and 22B are isometric views of a contoured sterilizing tool 900 according to still another embodiment of the present invention. As shown in FIGS. 22A and 22B, the contoured sterilizing tool 900 includes a contoured sterilizing element 904 transposed into and onto a single planar sheet 908 of a resilient material. The contoured sterilizing element 904 is transposed into the sheet 908 such that either or both sides of the contoured sterilizing tool 900 can be utilized for wiping and sterilizing a working end-site 912, 912' of a medical device 914, 914'. The contoured sterilizing tool 900 can be left on the medical device end-site 912, 912' to keep it sterile and clean until access is required.

The contoured sterilizing element 904 is transposed in the resilient, planar sheet 908 such that it defines a cavity 920 in an upper planar surface 922 of the planar sheet 908. The cavity 920 includes an inner surface 924 configured to receive a working end-site of a medical device therein such as, for example, the female-type working end-site 912 of a medical device 914 as shown in FIG. 22A. The inner surface 924 is configured to conform and contour to and to contact the outer and inner surfaces of the working end-end site 912 and, in some embodiments, can include any number of raised structures including ribs, threads, ridges, micropatterned features, microtextured features and the like configured to conform and to contact the surfaces to be sterilized. In some embodiments, the cavity 920 includes a base surface 926 including a raised base portion 928 configured to contact and to engage an inner surface of the working end-site of a medical device such as, for example, a lumen, a distal end and/or a septum. To accomplish this, the raised base portion 928 can have any number of configurations. For example, the raised base portion 928 can be configured as any one of a nipple, bump, nub, tine, or other similar projection.

The contoured sterilizing element 904 is transposed in the resilient, planar sheet 908 such that in addition to defining the cavity 920, the contoured sterilizing element 904 also defines an outwardly projecting portion 930. The outwardly projecting portion 930 projects away from the lower planar surface 932 of the resilient planar sheet 908. In some embodiments, the outwardly projecting portion 930 has an outer shape that complements the inner shape of the cavity 920. The outwardly projecting portion 930 includes an outer surface 934 shaped to conform and contour to and to contact the outer and inner surfaces of a medical device end-site such as, for example, the male-type working end-site 912' of a medical device 914' as shown in FIG. 22B. Additionally, the outer surface 934 of the outwardly projecting portion 930 can include any number of raised structures including ribs, threads, ridges, microtextured features, micropatterned features and the like configured to contact and conform to the surfaces to be sterilized. In some embodiments, the outwardly projecting portion 930 includes a recessed portion 938 shaped to receive the outer and inner surfaces of a working end-site of a medical device therein. In one embodiment, the recessed portion 938 has an exterior shape 942 that is transposed to complement an interior shape 944 of the raised base portion 928 formed as part of the cavity 920.

Figure 23:
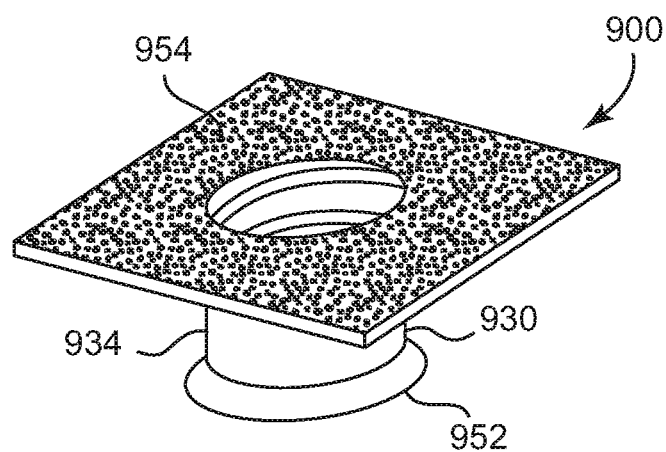
FIG. 23 is an isometric view of a contoured sterilizing tool according to yet another embodiment of the present invention.

FIG. 23 is an isometric view of a contoured sterilizing tool 900 according to further embodiments of the present invention. As shown in FIG. 23, the contoured sterilizing tool 900 can include a finger grip 952 formed on the outer surface 934 of the outwardly projecting portion 930. Additionally, the contoured sterilizing tool 900 can include a plurality of surface texturing features 954 formed on the upper planar surface 922 and/or lower planar surface 932 of the resilient planar sheet 908. The surface texturing features 954 can have any configuration designed to facilitate gripping of the tool 900 including, but not limited to, ridges, bumps, surface roughing, rings, concentric circles, lattice features and the like. The finger grip 952 and/or surface texturing features 954 are provided to facilitate gripping and manipulation of the tool 900 by the user.

Figure 24:
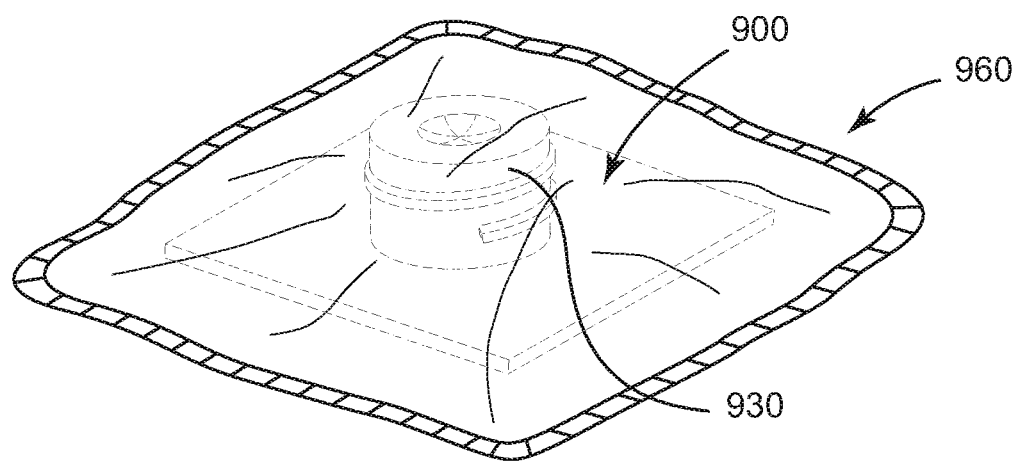
FIG. 24 is a schematic view of a contoured sterilizing tool provided in accordance with an embodiment of the present invention contained within a packaging.

FIG. 24 is a schematic view of a contoured sterilizing tool 900, such as described above in reference to FIGS. 22A-23, contained within a packaging 960. The packaging 960 is adapted to maintain a sterile and/or moisture-rich environment within the packaging 960 when the packing is sealed. In some embodiments, the packaging 960 is an easy-tear packaging that can be easily torn open by the user to access the sterilizing tool 900 contained within. In one embodiment, as shown, the contoured sterilizing tool 900 is adapted to be compressed to substantially flatten the transposed configuration within the packaging 960. When the packaging 960 is opened and the sterilizing tool 900 removed, the resiliency of the material used to fabricate the tool 900 facilitates the outward projecting portion 930 of the sterilizing tool 900 to re-expand to an uncompressed configuration ready for use as shown, for example, in either FIG. 22A or FIG. 22B.

According to various embodiments, the contoured sterilizing tool 900 can be fabricated from a resilient, planar sheet of material 908. The resilient planar sheet of material 908 can be selected from a wide variety of resilient materials of varying durometers and elasticity. Exemplary resilient materials include, but are not limited to silicones, rubbers including latex-free rubbers, viscoelastic foams, ethylene propylene diene monomer rubbers (EPDM) and other suitable materials known to those of skill in the art. In some embodiments, the contoured sterilizing tool 900 can be made of a translucent, transparent or optically clear resilient elastomeric material such as a silicone or a latex-free rubber. A translucent or optically clear sterilizing tool 900 assists the user in visualizing and to see-through a change in the appearance of either the working end-site and/or the sterilizing tool itself during the cleaning and sterilization of the working end-site.

The contoured sterilizing tool 900 including the contoured sterilizing element 904, as described above according to the various embodiments, can be transposed in the resilient, planar sheet 908 using a variety of manufacturing techniques. Exemplary techniques suitable for fabricating the sterilizing tool 900 include various molding methods such as transfer, compression or injection molding or other similar techniques. According to one embodiment, the contoured sterilizing element 904 can be pressed or molded into the resilient, planar sheet 908.

In several embodiments, the resilient material used to form the resilient, planar sheet 908 is impregnated with a liquid or dry anti-pathogenic agent, such as described in detail above, for applying an inclusive layer of an anti-pathogenic agent to the inner and outer surfaces of the working end-site of a medical device for sterilization. In some embodiments, the resilient planar sheet 908 can also be impregnated with a visual-change reactant. The visual-change reactant may cause the contoured sterilizing tool 900 and/or the working end-site to undergo a visual change indicating that the working end-site of the medical device has been adequately sterilized and is ready for use. For example, in one embodiment, the sterilizing tool 900 can be impregnated with a visual change reactant that when applied to the surface of the working end-site, causes the working end-site to change color. In a further embodiment, the visual change reactant undergoes an additional color change when the working-end site is dried. Exemplary agents suitable for this purpose include dyes, reactants, catalysts and other similar agents suitable for this purpose known to those of skill in the art.

In some embodiments, the contoured sterilizing tool 900 is made from a translucent or transparent material and provides a visual "see through" indication that the working end-site has received exposure from the anti-pathogenic agent contained within the contoured sterilizing tool 900, causing a visual discoloration of the working end-site and indicating that the working end-site has been sterilized and is ready for use. In some embodiments, the contoured sterilizing tool 900 impregnated with an anti-pathogenic agent releases the anti-pathogenic agent upon contact with the working end-site of the medical device, wetting the surface with the anti-pathogenic agent causing a visual change in the end-site due to a microporous (e.g., polymeric porous permeable polymer), micropatterned, bonded coating or solvatochromic dyed surface (e.g., merocyanine dye or Reichardt's dye) of the end-site. In another embodiment the translucent/transparent contoured sterilizing tool 900 itself can include a micropatterned (e.g., fine lines or cracks), microtextured or a microporous surface whereby refraction occurs when the wetted, "resilient" surface of the contoured sterilizing tool 900 contacts the "harder," more ridged surfaces of the end-site, causing a visual change to occur from a darker appearance when contact is first made (i.e. wetted) to a lighter appearance as when the sterilizing tool 900 is left in place on the working end-site and the anti-pathogenic agent dries and/or evaporates. In further embodiments, the sterilizing tool 900 visually changes from a first state to a second state or similarly from visually light to visually dark or from a dark to a light surface over time due to exposure to an anti-pathogenic agent, and from a wetted surface to a dry surface. In other embodiments, the sterilizing tool 900 undergoes a visual change in response to manual pressure applied to the tool 900. According to the various embodiments described above, the visual change can be a color change. In other embodiments, the micropattern or microtexturing provides an additional refinement to the contour sterilizing tool for contacting and cleaning intricate details on an end-site such as cracks, crevices or grooves and where microscopic bacterium can reside on an end-site and particularly where an end-site has been assemble with multiple components having microscopic surfaces that can harbor bacterium (e.g. needle-less connector having assembled components such as a housing, seals, valve or septum). The microtexturing or micropattern can be anyone of ridges, bumps, surface roughing, rings, concentric circles, lattice features and the like. In a further embodiment of the contour sterilizing element 900 can include a microporous surface adapted to retain a measured amount of an antipathogenic agent such that the sterilizing element 900 is adapted to apply an inclusive layer to an end-site in a manner to promote a fast drying rate. In yet another embodiment, the microporous surface is adapted to deliver a predetermined amount of anti-pathogenic agent for the purpose of leaving a measured amount of anti-pathogenic residue to maintain the sterility on the end-site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features. Accordingly, the scope of the present invention is intended to embrace all such alternatives, modifications, and variations as fall within the scope of the claims, together with all equivalents thereof.

What is claimed is:

1. A sterilizing device configured to couple onto a male luer end of a syringe, the male luer end having a threaded male luer shroud and a tapered male luer slip; the sterilizing device comprising:
  an elongated integrated housing comprising a first housing portion having a first cavity accessible through a first opening in the first housing portion from a first axial direction and a second housing portion having a second cavity accessible through a second opening in the second housing portion from a second axial direction opposite the first axial direction;

a partition separating the first cavity from the second cavity;

an article carrying an antipathogenic agent disposed within the first cavity, the article configured to structurally engage and disinfect an end-site of a medical device inserted through the first opening and into the first cavity;

a frangible lid or seal covering the first opening; and a form-fit connector disposed within the second cavity, the form-fit connector configured to secure to the male luer end of the syringe, the form-fit connector further having an inner cavity different from the second cavity and accessible through an access opening in the form-fit connector from the second axial direction configured to frictionally engage the tapered male luer slip of the syringe.

2. The sterilizing device of claim 1, wherein the form-fit connector is configured to threadably engage the threaded male luer shroud on the syringe.

3. The sterilizing device of claim 2, wherein the form-fit connector is a female luer.

4. The sterilizing device of claim 1, wherein the form-fit connector is secured to the partition.

5. The sterilizing device of claim 1, wherein the form-fit connector is configured to frictionally engage the male shroud of the syringe.

6. The sterilizing device of claim 1, wherein the second housing portion includes an inner lining with a textured surface configured to frictionally secure to the male luer end of the syringe.

7. The sterilizing device of claim 1, wherein the article comprises a die-cut, shaped, molded, or sculpted piece.

8. The sterilizing device of claim 1, wherein an end of the article is configured with a recess cavity to inwardly receive the end-site of the medical device therein.

9. The sterilizing device of claim 8, wherein the end of the article is shaped to contour and contact at least one of an outer surface and an inner surface of the end-site of the medical device.

10. The sterilizing device of claim 1, wherein the second cavity is bounded by an inner wall of the second housing portion, and a hollow cylindrical void space configured and arranged to accommodate insertion of the male luer end of the syringe into the void space is defined between the inner wall of the second housing and an outer surface of the form-fit connector.

11. The sterilizing device of claim 1, wherein the form-fit connector has a surface treated to enhance frictional engagement of the form fit connector to the male luer end of the syringe.

12. The sterilizing device of claim 1, wherein the form-fit connector is configured to friction fit with the male luer end of the syringe.

13. A sterilizing device configured to couple onto a male luer end of a syringe, the male luer end having a threaded male luer shroud and a tapered male luer slip; the sterilizing device comprising:

an elongated integrated body comprising:
a housing portion having a first cavity accessible through a first opening in the first housing portion from a first axial direction, and
a syringe connector having an inner cavity accessible through an access opening in the syringe connector from a second axial direction opposite the first axial direction;

a partition separating the first cavity from the inner cavity;

an article disposed within the first cavity, the article carrying an antipathogenic agent and defining a recess cavity, the recesses cavity configured to inwardly receive, structurally engage and disinfect a sidewall of an end-site of a medical device when the end-site is inserted through the first opening and received inwardly into the recess cavity; and a frangible lid or seal covering the first opening;

wherein the syringe connector is configured to secure to the male luer end of the syringe, with the inner cavity configured to frictionally engage the tapered male luer slip of the syringe.

14. The sterilizing device of claim 13, wherein (i) the elongated integrated body further comprises a second housing portion, (ii) the second housing portion has a second cavity accessible through a second opening in the second housing portion from the second axial direction, and (iii) the syringe connector is disposed within the second cavity.

15. The sterilizing device of claim 13, wherein the syringe connector is configured to threadably engage the threaded male luer shroud of the syringe.

16. The sterilizing device of claim 15, wherein the syringe connector is a female luer.

17. The sterilizing device of claim 13, wherein the syringe connector is secured to the partition.

18. The sterilizing device of claim 13, wherein the syringe connector is configured to frictionally engage the male shroud of the syringe.

19. The sterilizing device of claim 13, wherein the article comprises a die-cut, shaped, molded, or sculpted piece.

20. The sterilizing device of claim 13, wherein the tapered male luer slip has a first taper angle, the inner cavity is axially tapered at a second taper angle, and the first and second taper angles are the same.

21. The sterilizing device of claim 13, wherein the inner cavity is bounded by a surface treated to enhance frictional engagement of the syringe connector to the male luer slip of the syringe.

22. A sterilizing device configured to couple onto a male luer end of a syringe, the male luer end having a threaded male luer shroud and a tapered male luer slip; the sterilizing device comprising:

an axially elongated integrated body comprising:
a housing portion having a first cavity accessible through a first opening in the first housing portion from a first axial direction, and
a syringe connector having an inner cavity accessible through an access opening in the syringe connector from a second axial direction opposite the first axial direction;

a partition separating the first cavity from the inner cavity;

an article disposed within the first cavity, the article (i) carrying an antipathogenic agent, (ii) defining a recess cavity, the recess cavity configured to inwardly receive, structurally engage and disinfect a sidewall of an end-site of a medical device when the end-site is inserted through the first opening and received inwardly into the recess cavity, and (iii) removable from the first cavity through the first opening concomitant with removal of the end-site to which the article is structurally engaged from the first cavity through the first opening; and a frangible lid or seal covering the first opening;

wherein the syringe connector is configured to secure to the male luer end of the syringe, with the inner cavity configured to frictionally engage the tapered male luer slip of the syringe.

23. The sterilizing device of claim 22, wherein (i) the axially elongated integrated body further comprises a second housing portion, (ii) the second housing portion has a second cavity accessible through a second opening in the second housing portion from the second axial direction, and (iii) the syringe connector is disposed within the second cavity.

24. The sterilizing device of claim 22, wherein the tapered male luer slip has a first taper angle, the inner cavity is axially tapered at a second taper angle, and the first and second taper angles are the same.

25. The sterilizing device of claim 22, wherein the article is removable from the first cavity in an axial direction of the article out from the first cavity through the first opening.

26. A sterilizing device defining an axial axis and configured to couple onto a male luer end of a syringe, the male luer end having a threaded male luer shroud and a tapered male luer slip; the sterilizing device comprising:
    an axially elongated integrated body comprising:
        a housing portion having a first cavity accessible through a first opening in the first housing portion from a first axial direction, and
        a syringe connector having an inner cavity accessible through an access opening in the syringe connector from a second axial direction opposite the first axial direction;
    a partition separating the first cavity from the inner cavity;
    an article disposed within the first cavity, the article carrying an antipathogenic agent and defining a recess cavity, the recesses cavity configured to inwardly receive, structurally engage and disinfect a sidewall of an end-site of a medical device when the end-site is inserted through the first opening and received inwardly into the recess cavity; and
    a frangible lid or seal covering the first opening;
    wherein (i) the article and housing portion are detachable together as a unified unit from the syringe connector, (ii) the unified unit is operable for remaining structurally engaged with the medical end-site positioned within the first cavity and in structural engagement with the article throughout and subsequent to such detachment, (iii) the syringe connector is configured to secure to the male luer end of the syringe with the inner cavity configured to frictionally engage the tapered male luer slip of the syringe, and (iv) the syringe connector operable for remaining secured with the male luer end of the syringe to which the syringe connector is secured throughout and subsequent to such detachment of the unified unit from the syringe connector.

27. The sterilizing device of claim 26, wherein (i) the axially elongated integrated body further comprises a second housing portion, (ii) the second housing portion has a second cavity accessible through a second opening in the second housing portion from the second axial direction, and (iii) the syringe connector is disposed within the second cavity.

28. The sterilizing device of claim 26, wherein the tapered male luer slip has a first taper angle, the inner cavity is axially tapered at a second taper angle, and the first and second taper angles are the same.

29. The sterilizing device of claim 26, wherein the syringe connector and partition are attached to the housing portion along a frangible juncture whereby the syringe connector and the partition are detachable from the housing portion by the frangible juncture.

30. A sterilizing device configured to couple onto a male luer end of a syringe, the male luer end having a threaded male luer shroud and a tapered male luer slip; the sterilizing device comprising:
    an axially elongated integrated body comprising:
        a housing portion having a first cavity accessible through a first opening in the first housing portion from a first axial direction, and
        a syringe connector having an inner cavity accessible through an access opening in the syringe connector from a second axial direction opposite the first axial direction;
    a partition separating the first cavity from the inner cavity;
    an article disposed within the first cavity, the article (i) carrying an antipathogenic agent, (ii) defining a recess cavity, the recess cavity configured to inwardly receive, structurally engage and disinfect a sidewall of an end-site of a medical device when the end-site is inserted through the first opening and received inwardly into the recess cavity, and (iii) removable from the first cavity through the first opening concomitant with removal of an end-site of a medical device to which the article is structurally engaged from the first cavity through the first opening; and
    a frangible lid or seal covering the first opening;
    wherein the syringe connector is (i) configured to secure to the male luer end of the syringe with the inner cavity configured to frictionally engage the tapered male luer slip of the syringe, and (ii) detachable from the housing portion.

31. The sterilizing device of claim 30, wherein (i) the axially elongated integrated body further comprises a second housing portion, (ii) the second housing portion has a second cavity accessible through a second opening in the second housing portion from the second axial direction, and (iii) the syringe connector is disposed within the second cavity.

32. The sterilizing device of claim 30, wherein the tapered male luer slip has a first taper angle, the inner cavity is axially tapered at a second taper angle, and the first and second taper angles are the same.

33. The sterilizing device of claim 30, wherein the article is removable from the first cavity in an axial direction of the article out from the first cavity through the first opening.

34. The sterilizing device of claim 30, wherein the syringe connector is attached to the housing portion along a frangible juncture whereby the syringe connector and the housing portion are detachable from one another by the frangible juncture.

35. An integrated sterilizing device and syringe, comprising:
    a syringe having a male luer fitting at one end which includes a tapered male luer slip, a lumen through the male luer slip, and an internally threaded shroud around the male luer slip; and
    a sterilizing device capping the male luer fitting of the syringe, comprising:
        an elongated integrated body comprising:
            a housing portion having a first cavity accessible through a first opening in the first housing portion from a first axial direction, and
            a syringe connector having an inner cavity accessible through an access opening in the syringe connector from a second axial direction opposite the first axial direction;
        a partition separating the first cavity from the inner cavity;
        an article disposed within the first cavity, the article carrying an antipathogenic agent and defining a recess cavity, the recesses cavity configured to inwardly receive, structurally engage and disinfect a sidewall of an end-site of a medical device when the end-site is inserted through the first opening and received inwardly into the recess cavity; and a frangible lid or seal covering the first opening;

wherein the tapered male luer slip of the syringe is frictionally engaged within the inner cavity of the sterilizing device so as to interface with the lumen.

36. The integrated sterilizing device and syringe of claim 35 wherein the syringe is filled with a liquid.

37. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a partition separating the first cavity from the inner cavity;

an article (i) disposed within the first cavity, carrying an antipathogenic agent, and having a recess cavity configured to inwardly receive, structurally engage and disinfect an end-site of a medical device when the end-site is inserted through the first opening and received inwardly into the recess cavity, and (ii) removable from the first cavity through the first opening concomitant with removal of an end-site of a medical device to which the article is structurally engaged from the first cavity through the first opening; and a frangible lid or seal covering the first opening;

wherein the tapered male luer slip of the syringe is frictionally engaged within the inner cavity of the sterilizing device so as to engage the lumen.

38. The integrated sterilizing device and syringe of claim 37 wherein the syringe is filled with a liquid.

39. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector detachable from the housing portion and having an inner cavity accessible through an access opening in the syringe connector from a second axial direction opposite the first axial direction;

a partition separating the first cavity from the inner cavity;

an article disposed within the first cavity, the article carrying an antipathogenic agent and defining a recess cavity, the recess cavity configured to inwardly receive, structurally engage and disinfect an end-site of a medical device when the end-site is inserted through the first opening and received inwardly into the recess cavity; and a frangible lid or seal covering the first opening;

wherein the tapered male luer slip of the syringe is frictionally engaged within the inner cavity of the sterilizing device so as to interface and engage the lumen.

40. The integrated sterilizing device and syringe of claim 39 wherein the syringe is filled with a liquid.

41. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector detachable from the housing portion and having an inner cavity accessible through an access opening in the syringe connector from a second axial direction opposite the first axial direction;

a partition separating the first cavity from the inner cavity;

an article (i) disposed within the first cavity, carrying an antipathogenic agent, and having a recess cavity configured to inwardly receive, structurally engage and disinfect an end-site of a medical device when the end-site is inserted through the first opening and received inwardly into the recess cavity, and (ii) removable from the first cavity through the first opening concomitant with removal of an end-site of a medical device to which the article is structurally engaged from the first cavity through the first opening; and a frangible lid or seal covering the first opening;

wherein the tapered male luer slip of the syringe is frictionally engaged within the inner cavity of the sterilizing device so as to engage the lumen inner surface.

42. The integrated sterilizing device and syringe of claim 41 wherein the syringe is filled with a liquid.

43. A sterilizing device configured to couple onto a male luer end of a syringe, the male luer end having a threaded male luer shroud and a tapered male luer slip; the sterilizing device comprising:

an elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a partition separating the first cavity from the inner cavity;

an article disposed within the first cavity, the article carrying an antipathogenic agent and having a recess cavity, the recesses cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity; and a frangible lid or seal covering the first opening;

wherein the syringe connector is configured to secure to the male luer end of the syringe, with the inner cavity configured to frictionally engage the tapered male luer slip of the syringe.

44. A sterilizing device configured to couple onto a male luer end of a syringe, the male luer end having a threaded male luer shroud and a tapered male luer slip; the sterilizing device comprising:

an elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a grippable partition separating the first cavity from the inner cavity;

an article disposed within the first cavity, the article carrying an antipathogenic agent and defining a recess cavity, the recesses cavity configured to inwardly receive, structurally engage and disinfect a sidewall of an end-site of a medical device when the end-site is inserted through the first opening and received inwardly into the recess cavity; and a frangible lid or seal covering the first opening;

wherein the syringe connector is configured to secure to the male luer end of the syringe, with (i) the inner cavity configured to frictionally engage the tapered male luer slip of the syringe, and (ii) a distal end of the male luer end of the syringe in gripped seated contact with the grippable partition whereby bi-directional rotation of the syringe effects a corresponding bi-directional rotation of the sterilizing device including the article relative to an end-site of a medical device disposed within the recess cavity.

45. A sterilizing device configured to couple onto a male luer end of a syringe, the male luer end having a threaded male luer shroud and a tapered male luer slip; the sterilizing device comprising:

an elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a grippable partition separating the first cavity from the inner cavity;

an article disposed within the first cavity, the article carrying an antipathogenic agent and having a recess cavity, the recesses cavity with a sidewall comprising a contoured surface having at least one of a ridge, a flange, a thread and a step, to define a shape mutually complimentary to a shape of an end-site of a medical device, and configured to inwardly receive, structurally engage and disinfect the end-site when the end-site is inserted through the first opening and received inwardly into the recess cavity; and a frangible lid or seal covering the first opening;

wherein the syringe connector is configured to secure to the male luer end of the syringe, with (i) the inner cavity configured to frictionally engage the tapered male luer slip of the syringe, and (ii) a distal end of the male luer end of the syringe in gripped seated contact with the grippable partition whereby bi-directional rotation of the syringe effects a corresponding bi-directional rotation of the sterilizing device including the article relative to an end-site of a medical device disposed within the recess cavity.

46. A sterilizing device configured to couple onto a male luer end of a syringe, the male luer end having a threaded male luer shroud and a tapered male luer slip; the sterilizing device comprising:

an axially elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a partition separating the first cavity from the inner cavity;

an article disposed within the first cavity, the article (i) carrying an antipathogenic agent, (ii) having a recess cavity, the recess cavity with a sidewall comprising a contoured surface to define a shape mutually complimentary to a shape of an end-site of a medical device, and configured to inwardly receive and structurally engage to disinfect the end-site when the end-site is inserted through the first opening and received inwardly into the recess cavity, and (iii) removable from the first cavity through the first opening concomitant with removal of the end-site to which the article is structurally engaged from the first cavity through the first opening; and a frangible lid or seal covering the first opening;

wherein the syringe connector is configured to secure to the male luer end of the syringe, with the inner cavity configured to frictionally engage the tapered male luer slip of the syringe.

47. A sterilizing device configured to couple onto a male luer end of a syringe, the male luer end having a threaded male luer shroud and a tapered male luer slip; the sterilizing device comprising:

an axially elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a grippable partition separating the first cavity from the inner cavity;

an article disposed within the first cavity, the article (i) carrying an antipathogenic agent, (ii) defining a recess cavity, the recess cavity configured to inwardly receive, structurally engage and disinfect a sidewall of an end-site of a medical device when the end-site is inserted through the first opening and received inwardly into the recess cavity, and (iii) removable from the first cavity through the first opening concomitant with removal of the end-site to which the article is structurally engaged from the first cavity through the first opening; and a frangible lid or seal covering the first opening;

wherein the syringe connector is configured to secure to the male luer end of the syringe, with (i) the inner cavity configured to frictionally engage the tapered male luer slip of the syringe, and (ii) a distal end of the male luer end of the syringe in gripped seated contact with the grippable partition whereby bi-directional rotation of the syringe effects a corresponding bi-directional rotation of the sterilizing device including the article relative to an end-site of a medical device disposed within the recess cavity.

48. The sterilizing device of claim 47 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

49. A sterilizing device defining an axial axis and configured to couple onto a male luer end of a syringe, the male luer end having a threaded male luer shroud and a tapered male luer slip; the sterilizing device comprising:
    an axially elongated integrated body comprising:
        a housing portion having a first cavity accessible through a first opening in the first housing portion from a first axial direction, and
        a syringe connector having an inner cavity accessible through an access opening in the syringe connector from a second axial direction opposite the first axial direction;
    a partition separating the first cavity from the inner cavity;
    an article disposed within the first cavity, the article carrying an antipathogenic agent and having a recess cavity, the recesses cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity; and
    a frangible lid or seal covering the first opening;
    wherein (i) the article and housing portion are detachable together as a unified unit from the syringe connector, (ii) the unified unit is operable for remaining structurally engaged with the medical end-site positioned within the first cavity and in structural engagement with the article throughout and subsequent to such detachment, (iii) the syringe connector is configured to secure to the male luer end of the syringe with the inner cavity configured to frictionally engage the tapered male luer slip of the syringe, and (iv) the syringe connector operable for remaining secured with the male luer end of the syringe to which the syringe connector is secured throughout and subsequent to such detachment of the unified unit from the syringe connector.

50. A sterilizing device defining an axial axis and configured to couple onto a male luer end of a syringe, the male luer end having a threaded male luer shroud and a tapered male luer slip; the sterilizing device comprising:
    an axially elongated integrated body comprising:
        a housing portion having a first cavity accessible through a first opening in the first housing portion from a first axial direction, and
        a syringe connector having an inner cavity accessible through an access opening in the syringe connector from a second axial direction opposite the first axial direction;
    a grippable partition separating the first cavity from the inner cavity;
    an article disposed within the first cavity, the article carrying an antipathogenic agent and defining a recess cavity, the recesses cavity configured to inwardly receive, structurally engage and disinfect a sidewall of an end-site of a medical device when the end-site is inserted through the first opening and received inwardly into the recess cavity; and
    a frangible lid or seal covering the first opening;
    wherein (i) the article and housing portion are detachable together as a unified unit from the syringe connector, (ii) the unified unit is operable for remaining structurally engaged with the medical end-site positioned within the first cavity and in structural engagement with the article throughout and subsequent to such detachment, (iii) the syringe connector is configured to secure to the male luer end of the syringe with the inner cavity configured to frictionally engage the tapered male luer slip of the syringe, with a distal end of the male luer end of the syringe in gripped seated contact with the grippable partition whereby bi-directional rotation of the syringe effects a corresponding bi-directional rotation of the sterilizing device including the article relative to an end-site of a medical device disposed within the recess cavity, and (iv) the syringe connector operable for remaining secured with the male luer end of the syringe and the grippable partition operable for remaining in seated contact with the distal end of the male luer end of the syringe to which the syringe connector is secured throughout and subsequent to such detachment of the unified unit from the syringe connector.

51. The sterilizing device of claim 50 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

52. A sterilizing device configured to couple onto a male luer end of a syringe, the male luer end having a threaded male luer shroud and a tapered male luer slip; the sterilizing device comprising:
    an axially elongated integrated body comprising:
        a housing portion having a first cavity accessible through a first opening in the first housing portion from a first axial direction, and
        a syringe connector having an inner cavity accessible through an access opening in the syringe connector from a second axial direction opposite the first axial direction;
    a partition separating the first cavity from the inner cavity;
    an article disposed within the first cavity, the article (i) carrying an antipathogenic agent, (ii) having a recess cavity, the recess cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity, and (iii) removable from the first cavity through the first opening concomitant with removal of an end-site of a medical device to which the article is structurally engaged from the first cavity through the first opening; and
    a frangible lid or seal covering the first opening;
    wherein the syringe connector is (i) configured to secure to the male luer end of the syringe with the inner cavity configured to frictionally engage the tapered male luer slip of the syringe, and (ii) detachable from the housing portion.

53. A sterilizing device configured to couple onto a male luer end of a syringe, the male luer end having a threaded male luer shroud and a tapered male luer slip; the sterilizing device comprising:
an axially elongated integrated body comprising:
a housing portion having a first cavity accessible through a first opening in the first housing portion from a first axial direction, and
a syringe connector having an inner cavity accessible through an access opening in the syringe connector from a second axial direction opposite the first axial direction;
a grippable partition separating the first cavity from the inner cavity;
an article disposed within the first cavity, the article (i) carrying an antipathogenic agent, (ii) defining a recess cavity, the recess cavity configured to inwardly receive, structurally engage and disinfect a sidewall of an end-site of a medical device when the end-site is inserted through the first opening and received inwardly into the recess cavity, and (iii) removable from the first cavity through the first opening concomitant with removal of an end-site of a medical device to which the article is structurally engaged from the first cavity through the first opening; and
a frangible lid or seal covering the first opening;
wherein the syringe connector is (i) configured to secure to the male luer end of the syringe with the inner cavity configured to frictionally engage the tapered male luer slip of the syringe, and a distal end of the male luer end of the syringe in gripped seated contact with the grippable partition whereby bi-directional rotation of the syringe effects a corresponding bi-directional rotation of the sterilizing device including the article relative to an end-site of a medical device disposed within the recess cavity, and (ii) detachable from the housing portion.

54. The sterilizing device of claim 53 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

55. An integrated sterilizing device and syringe, comprising:
a syringe having a male luer fitting at one end which includes a tapered male luer slip, a lumen through the male luer slip, and an internally threaded shroud around the male luer slip; and
a sterilizing device capping the male luer fitting of the syringe, comprising:
an elongated integrated body comprising:
a housing portion having a first cavity accessible through a first opening in the first housing portion from a first axial direction, and
a syringe connector having an inner cavity accessible through an access opening in the syringe connector from a second axial direction opposite the first axial direction;
a partition separating the first cavity from the inner cavity;
an article disposed within the first cavity, the article carrying an antipathogenic agent and having a recess cavity, the recesses cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity; and
a frangible lid or seal covering the first opening;
wherein the tapered male luer slip of the syringe is frictionally engaged within the inner cavity of the sterilizing device so as to interface with the lumen.

56. An integrated sterilizing device and syringe, comprising:
a syringe having a male luer fitting at one end which includes a tapered male luer slip, a lumen through the male luer slip, and an internally threaded shroud around the male luer slip; and
a sterilizing device capping the male luer fitting of the syringe, comprising:
an elongated integrated body comprising:
a housing portion having a first cavity accessible through a first opening in the first housing portion from a first axial direction, and
a syringe connector having an inner cavity accessible through an access opening in the syringe connector from a second axial direction opposite the first axial direction;
a grippable partition separating the first cavity from the inner cavity;
an article disposed within the first cavity, the article carrying an antipathogenic agent and defining a recess cavity, the recesses cavity configured to inwardly receive, structurally engage and disinfect an end-site of a medical device when the end-site is inserted through the first opening and received inwardly into the recess cavity; and
a frangible lid or seal covering the first opening;
wherein (i) the tapered male luer slip of the syringe is frictionally engaged within the inner cavity of the sterilizing device so as to interface with the lumen, and (ii) a distal end of the male luer end of the syringe is in gripped seated contact with the grippable partition whereby bi-directional rotation of the syringe effects a corresponding bi-directional rotation of the sterilizing device including the article relative to an end-site of a medical device disposed within the recess cavity.

57. The integrated sterilizing device of claim 56 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

58. An integrated sterilizing device and syringe, comprising:
a syringe having a male luer fitting at one end which includes a tapered male luer slip, a lumen through the male luer slip, and an internally threaded shroud around the male luer slip; and
a sterilizing device capping the male luer fitting of the syringe, comprising:
an axially elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a partition separating the first cavity from the inner cavity;

an article (i) disposed within the first cavity, carrying an antipathogenic agent, and having a recess cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity, and (ii) removable from the first cavity through the first opening concomitant with removal of an end-site of a medical device to which the article is structurally engaged from the first cavity through the first opening; and a frangible lid or seal covering the first opening;

wherein the tapered male luer slip of the syringe is frictionally engaged within the inner cavity of the sterilizing device so as to engage the lumen.

59. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector having an inner cavity accessible through an access opening in the syringe connector from a second axial direction opposite the first axial direction;

a grippable partition separating the first cavity from the inner cavity;

an article (i) disposed within the first cavity, carrying an antipathogenic agent, and defining a recess cavity configured to inwardly receive, structurally engage and disinfect an end-site of a medical device when the end-site is inserted through the first opening and received inwardly into the recess cavity, and (ii) removable from the first cavity through the first opening concomitant with removal of an end-site of a medical device to which the article is structurally engaged from the first cavity through the first opening; and a frangible lid or seal covering the first opening;

wherein (i) the tapered male luer slip of the syringe is frictionally engaged within the inner cavity of the sterilizing device so as to engage the lumen, and (ii) a distal end of the male luer end of the syringe is in gripped seated contact with the grippable partition whereby bi-directional rotation of the syringe effects a corresponding bi-directional rotation of the sterilizing device including the article relative to an end-site of a medical device disposed within the recess cavity.

60. The integrated sterilizing device of claim 59 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

61. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector detachable from the housing portion and having an inner cavity accessible through an access opening in the syringe connector from a second axial direction opposite the first axial direction;

a partition separating the first cavity from the inner cavity;

an article (i) disposed within the first cavity, the article carrying an antipathogenic agent and having a recess cavity, the recess cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity; and a frangible lid or seal covering the first opening;

wherein the tapered male luer slip of the syringe is frictionally engaged within the inner cavity of the sterilizing device so as to interface and engage the lumen.

62. An integrated sterilizing device and syringe, comprising:

a syringe having a male luer fitting at one end which includes a tapered male luer slip, a lumen through the male luer slip, and an internally threaded shroud around the male luer slip; and a sterilizing device capping the male luer fitting of the syringe, comprising:

an axially elongated integrated body comprising:

a housing portion having a first cavity accessible through a first opening in the first housing portion from a first axial direction, and a syringe connector detachable from the housing portion and having an inner cavity accessible through an access opening in the syringe connector from a second axial direction opposite the first axial direction;

a grippable partition separating the first cavity from the inner cavity;

an article disposed within the first cavity, the article carrying an antipathogenic agent and defining a recess cavity, the recess cavity configured to inwardly receive, structurally engage disinfect an end-site of a medical device when the end-site is inserted through the first opening and received inwardly into the recess cavity; and a frangible lid or seal covering the first opening;

wherein (i) the tapered male luer slip of the syringe is frictionally engaged within the inner cavity of the sterilizing device so as to interface and engage the lumen, and (ii) a distal end of the male luer end of the syringe is in gripped seated contact with the grippable partition whereby bi-directional rotation of the syringe effects a corresponding bi-directional rotation of the sterilizing device including the article relative to an end-site of a medical device disposed within the recess cavity.

63. The integrated sterilizing device of claim 62 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

64. An integrated sterilizing device and syringe, comprising:
   a syringe having a male luer fitting at one end which includes a tapered male luer slip, a lumen through the male luer slip, and an internally threaded shroud around the male luer slip; and
   a sterilizing device capping the male luer fitting of the syringe, comprising:
      an axially elongated integrated body comprising:
         a housing portion having a first cavity accessible through a first opening in the first housing portion from a first axial direction, and
         a syringe connector detachable from the housing portion and having an inner cavity accessible through an access opening in the syringe connector from a second axial direction opposite the first axial direction;
      a partition separating the first cavity from the inner cavity;
      an article disposed within the first cavity, the article (i) carrying an antipathogenic agent, (ii) having a recess cavity with a sidewall comprising a contoured surface to define a shape mutually complimentary to a shape of an end-site of a medical device, and configured to inwardly receive, structurally engage and disinfect the end-site when the end-site is inserted through the first opening and received inwardly into the recess cavity, and (iii) removable from the first cavity through the first opening concomitant with removal of the end-site of a medical device to which the article is structurally engaged from the first cavity through the first opening; and
      a frangible lid or seal covering the first opening;
   wherein the tapered male luer slip of the syringe is frictionally engaged within the inner cavity of the sterilizing device so as to engage the lumen inner surface.

65. An integrated sterilizing device and syringe, comprising:
   a syringe having a male luer fitting at one end which includes a tapered male luer slip, a lumen through the male luer slip, and an internally threaded shroud around the male luer slip; and
   a sterilizing device capping the male luer fitting of the syringe, comprising:
      an axially elongated integrated body comprising:
         a housing portion having a first cavity accessible through a first opening in the first housing portion from a first axial direction, and
         a syringe connector detachable from the housing portion and having an inner cavity accessible through an access opening in the syringe connector from a second axial direction opposite the first axial direction;
      a grippable partition separating the first cavity from the inner cavity;
      an article (i) disposed within the first cavity, carrying an antipathogenic agent, and having a recess cavity configured to inwardly receive, structurally engage and disinfect an end-site of a medical device when the end-site is inserted through the first opening and received inwardly into the recess cavity, and (ii) removable from the first cavity through the first opening concomitant with removal of an end-site of a medical device to which the article is structurally engaged from the first cavity through the first opening; and
      a frangible lid or seal covering the first opening;
   wherein (i) the tapered male luer slip of the syringe is frictionally engaged within the inner cavity of the sterilizing device so as to engage the lumen inner surface, and (ii) a distal end of the male luer end of the syringe is in gripped seated contact with the grippable partition whereby bi-directional rotation of the syringe effects a corresponding bi-directional rotation of the sterilizing device including the article relative to an end-site of a medical device disposed within the recess cavity.

66. The integrated sterilizing device of claim 65 wherein the recesses cavity has a sidewall comprising a contoured surface to define a shape mutually complimentary to a shape of the end-site of the medical device, the shape of the recess cavity sidewall effective to structurally engage and disinfect the sidewall of the end-site of the medical device when the end-site is inserted through the first opening and received inwardly into the recess cavity.

* * * * *